(12) United States Patent
Martin et al.

(10) Patent No.: US 12,257,101 B2
(45) Date of Patent: Mar. 25, 2025

(54) SYSTEM AND METHOD FOR DETERMINING CARDIAC RHYTHM AND/OR RESPIRATORY RATE

(71) Applicant: ECOLE DE TECHNOLOGIE SUPERIEURE, Montreal (CA)

(72) Inventors: Alexis Martin, Montreal (CA); Jeremie Voix, Montreal (CA)

(73) Assignee: ECOLE DE TECHNOLOGIE SUPERIEURE, Montreal (CA)

( * ) Notice: Subject to any disclaimer, the term of this patent is extended or adjusted under 35 U.S.C. 154(b) by 627 days.

(21) Appl. No.: 16/612,622

(22) PCT Filed: Apr. 13, 2018

(86) PCT No.: PCT/CA2018/050453
§ 371 (c)(1),
(2) Date: Nov. 11, 2019

(87) PCT Pub. No.: WO2018/205013
PCT Pub. Date: Nov. 15, 2018

(65) Prior Publication Data
US 2020/0196977 A1    Jun. 25, 2020

Related U.S. Application Data

(60) Provisional application No. 62/504,258, filed on May 10, 2017.

(51) Int. Cl.
*A61B 5/00* (2006.01)
*A61B 5/024* (2006.01)
(Continued)

(52) U.S. Cl.
CPC ............ *A61B 7/04* (2013.01); *A61B 5/02444* (2013.01); *A61B 5/7203* (2013.01); *A61B 5/725* (2013.01);
(Continued)

(58) Field of Classification Search
CPC ..... A61B 7/04; A61B 5/02444; A61B 5/7203; A61B 5/725; A61B 7/003; G16H 50/20; G16H 50/30; G16H 40/63
See application file for complete search history.

(56) References Cited

U.S. PATENT DOCUMENTS 6,741,707 B2    5/2004  Ray et al.
2008/0146890 A1*  6/2008  LeBoeuf ............... A61N 1/325
                                                     600/300
(Continued)

FOREIGN PATENT DOCUMENTS

EP          3010249 A1    4/2016
KR      20160097862 A     8/2016
(Continued)

OTHER PUBLICATIONS

Extended European Search Report issued on Jan. 11, 2021 from the corresponding European Patent Application No. 18798090.9.
International Search Report issue on Jul. 13, 2018 from the corresponding International Patent Application PCT/CA2018/050453.

*Primary Examiner* — Andrey Shostak
(74) *Attorney, Agent, or Firm* — Brouillette Legal Inc.; Philippe Brouillette

(57) ABSTRACT

A system and a method to determine heart and/or breathing rates. The system comprises a shell configured to occlude an ear canal, an in-ear microphone located inside the shell to capture an audio signal inside the ear canal, and a processor operatively connected to the in-ear microphone, the processor being configured to analyse the audio signal in order to determine at least one of a heart beat and/or a respiration rate measurement or attribute, even when the wearer of the system is immersed in high level of environmental noise. The system and method also comprise the use of an adaptive digital filter to remove the residual environmental noise from the audio signal captured by the in-ear microphone. The system and method also comprise the use of a prede- (Continued)

termined audio signal association to identify attributes of the captured audio signal inside the ear canal.

8 Claims, 26 Drawing Sheets

(51) Int. Cl.
  *A61B 7/00* (2006.01)
  *A61B 7/04* (2006.01)
  *G16H 50/20* (2018.01)
  *G16H 50/30* (2018.01)
(52) U.S. Cl.
  CPC ............ *A61B 7/003* (2013.01); *G16H 50/20* (2018.01); *G16H 50/30* (2018.01)

(56) References Cited

U.S. PATENT DOCUMENTS

| | | | |
|---|---|---|---|
| 2012/0130263 A1* | 5/2012 | Pretorius | A61B 5/349 600/509 |
| 2016/0192050 A1* | 6/2016 | Masaki | H04R 1/1058 381/74 |
| 2016/0212530 A1* | 7/2016 | Liu | H04R 1/1091 |
| 2016/0228092 A1* | 8/2016 | Kim | G01S 7/5208 |
| 2016/0296799 A1 | 10/2016 | Macagnano et al. | |
| 2020/0260962 A1* | 8/2020 | Mouchantaf | A61B 5/4809 |

FOREIGN PATENT DOCUMENTS

| | | |
|---|---|---|
| WO | WO03088841 A2 | 10/2003 |
| WO | WO2009069037 A2 | 6/2009 |

\* cited by examiner

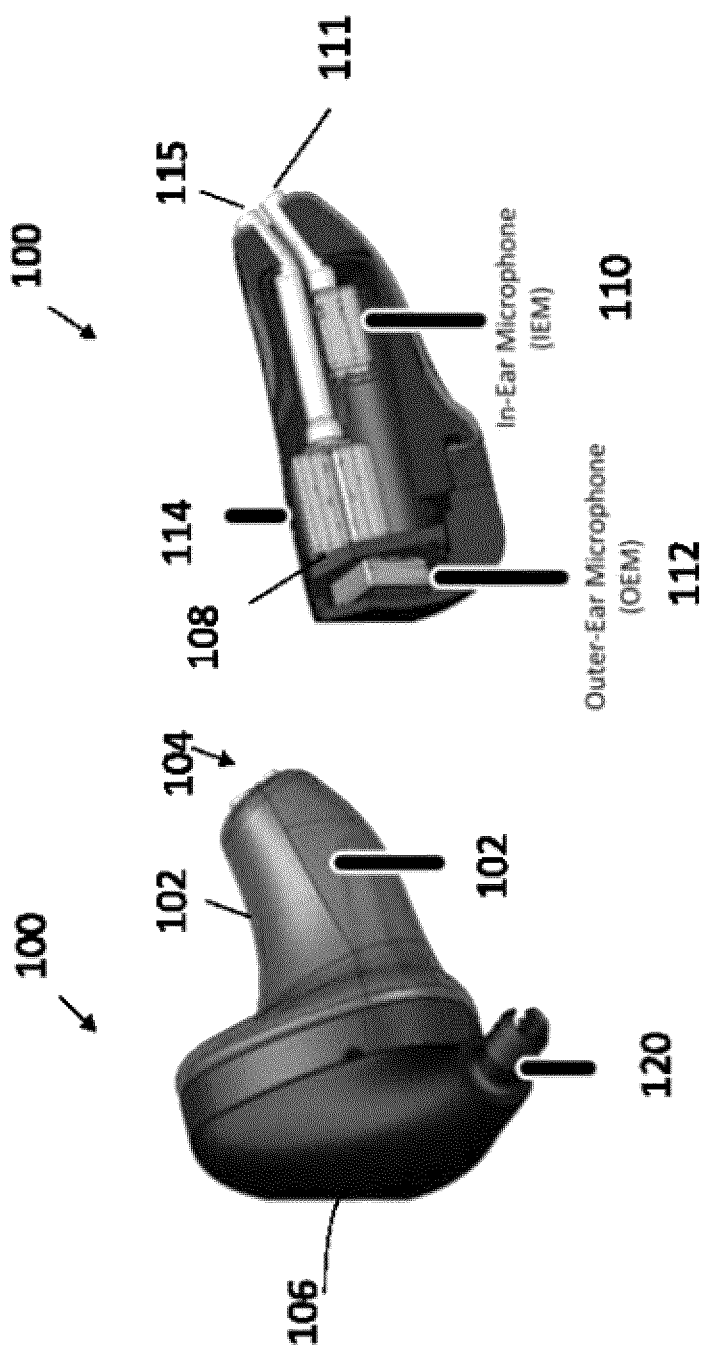

SYSTEM AND METHOD FOR DETERMINING CARDIAC RHYTHM AND/OR RESPIRATORY RATE

CROSS-REFERENCE TO RELATED APPLICATIONS

The present patent application claims the benefits of priority of U.S. Provisional Patent Application No. 62/504,258, entitled "System and method for determining cardiac rhythm and respiratory rate" and filed at the United States Patent and Trademark Office on May 10, 2017, the content of which is incorporated herein by reference.

FIELD OF THE INVENTION

The present invention generally relates to health monitoring and in particular to systems and methods for measuring cardiac rhythm and/or respiratory rate.

BACKGROUND OF THE INVENTION

Continuous health monitoring facilitates detecting any sudden change in a person's physiological signals. In particular, sudden change in heart rate or breathing rate may be caused by an accident or sudden illness, or onset of a disease. Such continued health monitoring may be needed for an increasingly aging population or industrial workers.

Non-invasive health monitoring methods are widely used in clinical applications to monitor physiological parameters such as heart rate or breathing rate. Systems such as electrocardiogramography, and spirography may be accurate but are often bulky to wear.

There is thus a need for a new health monitoring system that is lighter to wear and easier to use.

In Kaufmann, A. Malhotra, M. Ryschka, S. Kusche, G. Ardelt, N. Hunsche, and K. Breisslein, "*A System for In-Ear Pulse Wave Measurements*", Biomedical Engineering-Biomedizinische Technik, vol. 59, pp. S887-S890, 2014 (hereafter "Kaufmann et al."), there was created an experimental prototype consisting of a microphone located outside the ear with a tube passing through an earplug. A Kaufmann's algorithm was developed to detect heartbeats to calculate the transient time of the wave between the heart and the ear. However, such Kaufmann's algorithm may only be used in a no-noise environment. Kaufmann's algorithm provided calculation of heartbeat and did not describe breathing rate extraction. Unfortunately, validation was made using a very small data set and the protocol was not explicit. It is possible that the subject breathed very lightly to make heartbeat detection easier given that breathing generates low frequency artefacts.

G. A. Pressler, J. P. Mansfield, H. Pasterkamp, and G. R. Wodicka, "*Detection of respiratory sounds at the external ear,*" IEEE Transactions on Biomedical Engineering, vol. 51, no. 12, pp. 2089-2096, 2004 (hereafter "Pressler et al.") measured respiration sounds on 20 subjects with a microphone located inside an earplug and showed that the ear is a promising location to detect respiration. However, no specific algorithms were developed to extract breathing rate. Moreover, the total duration of recorded signals was short and the hardware used for acquisition is now obsolete. No database currently exists of sounds measured in the ear canal with signals sufficiently long in duration and representative of real-world conditions.

SUMMARY OF THE INVENTION

The shortcomings of the identified prior art may be generally mitigated by a system and method for determining cardiac rhythm and respiratory rate as described herein.

Such system and method may be used for non-invasive medical monitoring. It may be integrated in various intra-auricular devices such as earplugs, earphones or hearing aids. The system and method may be used for monitoring of vital signs of a person, such as, but not limited to elderly people through their hearing aids or for monitoring industrial workers through their hearing protection devices.

According to one aspect, there is a system for measuring a heart rate and a breathing rate, the system comprises a shell configured to at least partially occlude or obstruct an ear canal from the environment outside the ear canal. The system further comprises an in-ear microphone (IEM) located inside the shell and configured to capture an audio signal inside the ear canal. The system also comprises a processing device operatively connected to the IEM, the processing device is configured to analyze the audio signal in order to determine at least one of a heart beat (also referred to herein as "cardiac rhythm" and also as "heart rate") and/or a respiration rate (also referred to herein as "breathing rate").

According to another aspect, there is a method for determining an attribute of a heart rate or a breathing rate. The method comprises capturing at least one inner audio signal inside an ear canal of a user with an in-ear microphone. Then processing the at least one inner audio signal and identifying at least one attribute of the at least one inner audio signal according to a predetermined audio signal association, the at least one attribute is associated to at least one of a heart rate or a breathing rate.

According to yet another aspect, there is a method for determining a heart rate or breathing rate. The method comprises capturing at least one inner audio signal inside an ear canal of a user with an in-ear microphone. Then extracting at least one of a heart rate and a breathing rate from the at least one inner audio signal and determining at least one measurement of the extracted at least one of a heart rate and a breathing rate.

According to some embodiments, the system may comprise an audio recorder operatively connected to the in-ear microphone and configured to record the audio signal captured by the in-ear microphone The system may further comprise an outer-ear microphone (OEM) configured to capture environment audio signal (e.g. sounds outside of the ear canal). The environment audio signal captured by the outer-ear microphone may be used for denoising the audio signal captured by the in-ear microphone, as described herein.

The system may further comprise a loudspeaker located inside the shell, the loudspeaker being configured to reproduce, inside the ear canal, the audio signal captured by the outer-ear microphone. For instance, the audio signal captured by the outer-ear microphone and then reproduced by a loudspeaker may be attenuated or otherwise modified by an internal loudspeaker controller that may be located, for instance, inside the shell. In an alternate embodiment or in combination, the loudspeaker may also be used to play back music, to receive communication signals or to play warning signals to the wearer of the system.

The system may further comprise a database configured to store the recorded audio signal. This database may also be used for automated identification of the audio signal captured by IEM.

The system may further comprise a monitoring device configured to receive the measured and determined cardiac rate and the respiratory rate. The system may further comprise a display configured to display the cardiac rate and the respiratory rate. The monitoring device or the display may be remotely located from the system. Indeed, the system may be adapted to send such cardiac or respiratory information to a remote display or a remote monitoring device. In telemedicine applications, a medical or paramedical person can thereby monitor a patient from a remote location.

The method for determining a heart rate or a breathing rate may further comprise the steps of downsampling the captured and recorded audio signal, obtaining a data window of several seconds, and analyzing the data window in order to extract the heart and breathing rates.

The method may further comprise the step of transmitting the heart beat and breathing rates to the monitoring device.

Extracting the heart and breathing rates from the measured audio signal as described herein may be performed using signal processing methods, and therefore may be realized using digital signal processing (DSP) devices. Alternatively, extracting the heart and breathing rates from the measured audio signal may be performed on a computer processor.

Extracting the heart rate and extracting breathing rate from the measured audio signal may be performed by similar method steps, while adapting the frequency ranges and downsampling factors to the breathing rate extraction or cardiac extraction, respectively.

Extracting the heart rate and extracting breathing rate from IEM signal captured inside the occluded ear canal may comprise the following steps: applying a first band pass filter, applying a Hilbert transform to extract the envelope of the temporal audio signal, determining a center frequency of the pass-band filter (Fc), applying a second band pass filter, and extracting the peaks of the data. These steps may be performed simultaneously for the heart rate and breathing rate. Extracting the heart rate and extracting breathing rate may further comprise: a first decimation before applying the first band pass filter, and a second decimation before determining the center frequency of the second band-pass filter.

The method may further comprise the step of denoising the acoustic biosignals measured inside the ear canal. The denoising may permit using the method for determining the heart rate and beat rate in noisy conditions, i.e. when the system is used in high level of ambient noise. The denoising process removes the residual environmental noise that is present under the earpiece in the occluded ear canal.

For instance, the denoising may be performed using an adaptive filter. According to some embodiments, the adaptive filter may be tuned using a Normalize Least Mean Square error (nLMS) approach and taking the OEM signal as the reference for the disturbance signal, such as the adaptive filter described in U.S. Provisional Patent application Ser. No. 62/332,861, content of which is incorporated herein by reference. The adaptive filter can be optimized to the denoising of the biosignals by applying higher relative weights for the filter coefficients of the adaptive filter at the lower frequencies, where the biosignals are present.

Advantageously, the system and methods as described herein may permit to determine the cardiac rhythm or respiratory rate even if the person (user, wearer of the earpiece) is located in a noisy environment. For instance, the method may be used when the environmental noise is approximately up to 110 dB SPL (Sound Pressure Level).

In some embodiments, the system and methods as described herein may provide not only passive isolation of the IEM microphone, but also removal of the residual noise by adaptive filtering.

In some embodiments, the system and the method for determining a heart rate or breathing rate or the method for determining an attribute of a heart rate or breathing rate as described herein may be used in a noisy environment due to data captured by both the in-ear microphone (IEM) and the outer-ear microphone (OEM).

The method and system as described herein may be used in a wide range of non-invasive vital signs monitoring applications, such as monitoring workers in hazardous and noisy environments. For instance, the method and system as described herein may be used for monitoring heart and breathing rates of workers in heavy industry, construction, mining, or monitoring firefighters.

Other and further aspects and advantages of the present invention will be obvious upon an understanding of the illustrative embodiments about to be described or will be indicated in the appended claims, and various advantages not referred to herein will occur to one skilled in the art upon employment of the invention in practice.

BRIEF DESCRIPTION OF THE DRAWINGS

The above and other aspects, features and advantages of the invention will become more readily apparent from the following description, reference being made to the accompanying drawings in which:

FIG. 1A shows a perspective view of an earpiece, in accordance with at least one embodiment;

FIG. 1B shows a sliced view of the earpiece, showing electroacoustic components inside the earpiece, in accordance with at least one embodiment;

DETAILED DESCRIPTION OF THE PREFERRED EMBODIMENT

A novel system and method for measurement of heart and breathing rates will be described hereinafter. Although the invention is described in terms of specific illustrative embodiments, it is to be understood that the embodiments described herein are by way of example only and that the scope of the invention is not intended to be limited thereby.

An in-ear microphone may be inserted into an occluded ear canal of a person and a cardiac rhythm or a respiratory rate (breathing rate) of the person may be measured. Sounds produced by the heart or the breathing of the person may be captured by the microphone placed in the ear canal. The captured sound may be analysed to determine a cardiac rhythm or respiratory rate.

It should be noted that the term "heart sounds" as used herein comprises sounds indicative of heart beats. For instance, such sounds may be generated by the pulse waves propagated through the body of the user.

It should be noted that the terms "audio signal" and "sound" are used herein interchangeably. The term "algorithm" may refer to the method as described herein and/or any portion of the method as described herein.

Figure 1C:
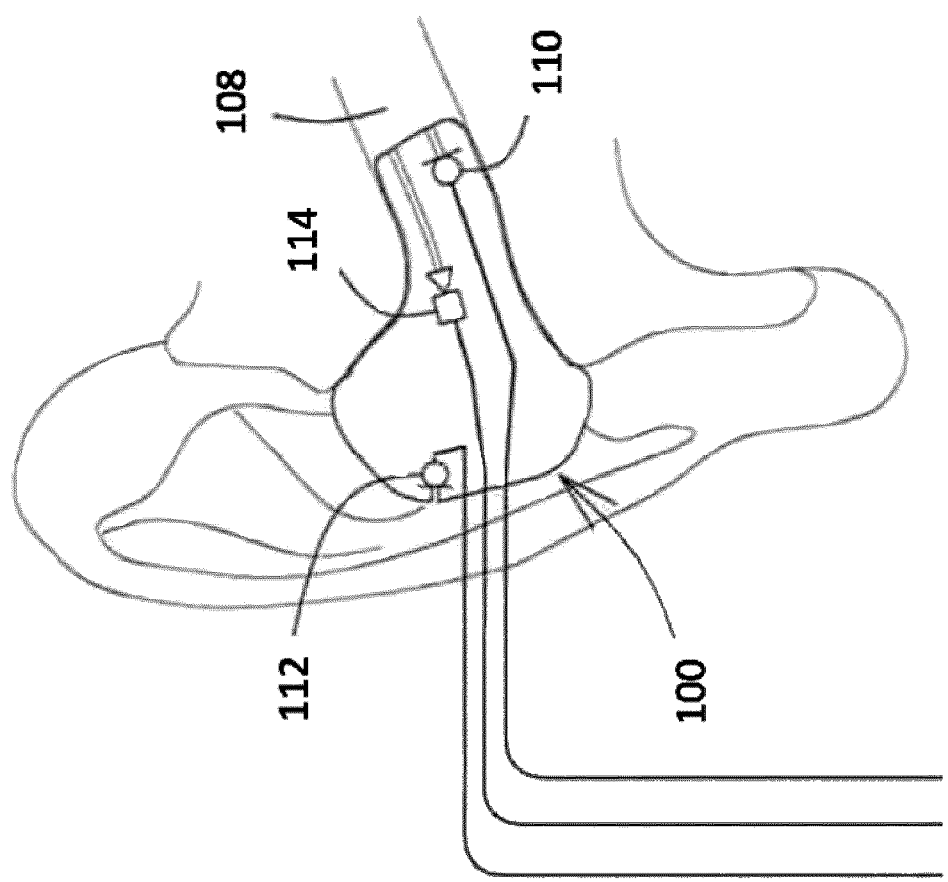
FIG. 1C shows a schematic view of the earpiece, showing electroacoustic components inside the earpiece, in accordance with at least one embodiment.

Referring now to FIGS. 1A and 1B, shown therein is an embodiment of the (instrumented) earpiece 100 comprising a shell 102, an in-ear microphone 110 and an outer-ear microphone 112 both located inside the shell 102. The earpiece 100 may also comprise a loudspeaker 114 as shown at FIG. 1B. FIG. 1A shows a perspective view of an exemplary intra-aural earpiece 100 and FIG. 1B shows exemplary electroacoustic components located inside the earpiece 100.

The shell 102 is configured to occlude (obstruct) an ear canal of the user from the environment outside the ear canal. The shell has an ear-side 104 that is configured to fit inside the user's ear canal and an outer-side 106.

Referring now to FIG. 1B, an in-ear microphone (IEM) 110 is located inside the shell 102 and is configured to capture (and optionally record) sounds inside the ear canal of the user. An in-ear microphone canal 111 leads from the ear canal to the IEM 110. As shown, FIG. 1B, an aperture of the in-ear microphone canal 111 is suspended in the ear canal of the user when the shell 102 is worn by the said user. The in-ear microphone 110 is located behind an earplug separator 108 and takes advantage of its passive acoustic attenuation. For instance, one or more earplug separators 108 may divide the shell 102 into to cavities.

The outer-ear microphone (OEM) 112 is configured to capture environment sounds (sounds outside of the ear canal). As shown at FIG. 1B, the OEM 112 is located on the outer side of the earplug separator 108.

A speaker (also referred herein as the "loudspeaker", to avoid confusing with human talking) 114 may be located inside the shell 102 and may be configured to reproduce, inside the ear canal of the user, the sounds captured by the outer-ear microphone 112. As shown at FIG. 1B, the sound from the loudspeaker 114 may be lead to the ear canal of the user through the loudspeaker canal 115.

For instance, the sound captured by the OEM may be attenuated or otherwise modified (e.g. by modifying sound at specific frequencies).

It should be understood that more than one loudspeaker 114 and more than two microphones, as well as other electroacoustic components may be installed in the earpiece 100.

Figure 15A:
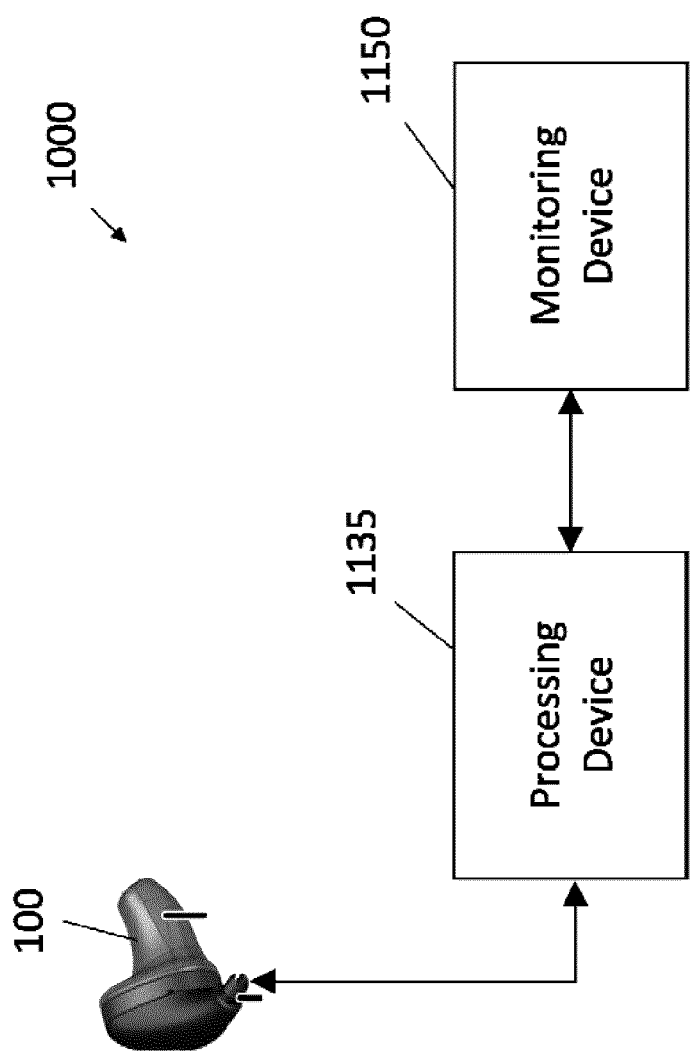
FIG. 15A shows a system for measurement of heart and breathing rates, in accordance with at least one embodiment.

Referring now to FIG. 15A, an embodiment of a system 1000 for measurement of heart and breathing rates is shown. The system 1000 comprises an earpiece 100, a processing device 1135, and a monitoring device 1150.

Figure 15B:
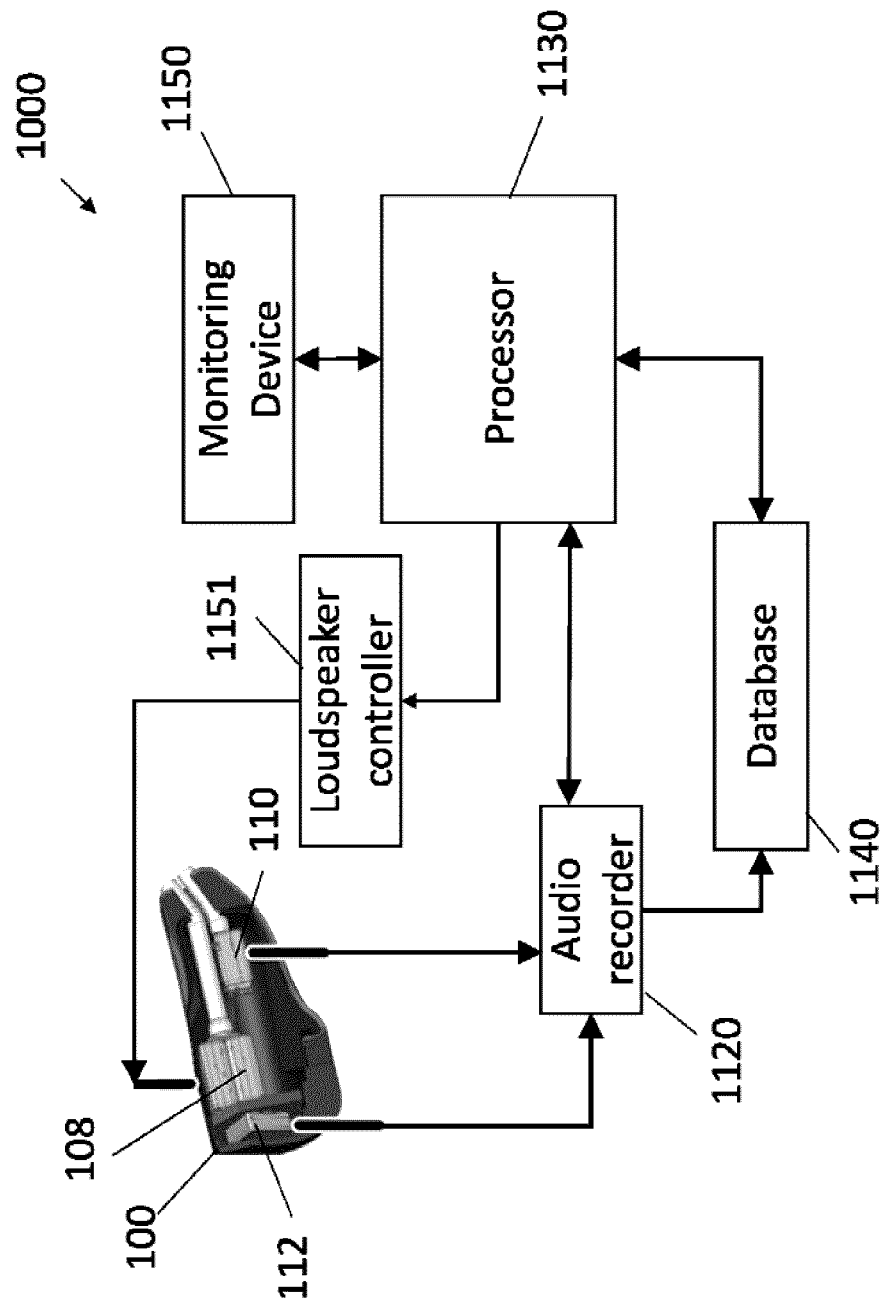
FIG. 15B shows the system for measurement of heart and breathing rates, in accordance with at least one embodiment.

According to some embodiments, as presented in FIGS. 15B, the processing device 1135 of FIG. 15A comprises an audio recorder 1120 and a processor 1130. The processor 1130 may be configured to determine at least one of a heart beat (also referred herein as "heart rate") and a respiration (breathing) rate from the data received from the earpiece 100.

In some embodiments, the earpiece 100 is operatively connected to an audio recorder 1120. After the sound is captured by the IEM 110, the sound may be transmitted to the audio recorder 1120 for recording. Audio data may be recorded with a multichannel digital audio recorder 1120 at a given sample rate.

For instance, as shown at FIGS. 1A and 15B, the earpiece 100 may be connected to the audio recorder 1120 using a wired link through an earpiece output 120. In another embodiment, the earpiece 100 may be connected to the audio recorder 1120 using a wireless link. For instance, the earpiece 100 may further comprise an antenna for this purpose.

The earpiece 100 may have disposable tips. The tips may be made, for instance, from a foam.

In an alternative embodiment, the audio recorder 1120 may be located inside the earpiece 100 and may comprise various devices as described herein.

The monitoring device 1150 may be any device that may need to receive and/or further process the measured heart and breathing rates of the user. For instance, the monitoring device 1150 may be a server that may collect information on the user's health. Moreover, the monitoring device 1150 may have a display for displaying the heart and breathing rate.

With reference to FIGS. 15A, it should be understood that the earpiece 100, the processing device 1135, and/or monitoring device 1150 may be all located in the same device, or may be separate devices being wirelessly connected, or may be separate devices connected using wires. Moreover, various devices may be part of the processing device 1135, such as presented in FIG. 15B, and the processing device 1135 may be located on or inside the earpiece 100.

For instance, the monitoring device 1150 may receive information from the processing device 1135 and transmit a feedback back to the processing device 1135. The processing device 1135 may also send a feedback back to the earpiece 100.

In some embodiments, the processor 1130 may transmit the values of the heart rate (for instance, "95" or "95 BPM") and respiration rate (for instance, "10", or "10 CPM") to the monitoring device 1150. For instance, when used for external monitoring of workers, the monitoring device 1150 may be located remotely such as at a supervision station and the heart rate and respiration rate may be sent to the monitoring device 1150. This way, monitoring of the heart rate and respiration rate associated to each worker is performed remotely.

The recorded sounds may be collected and stored temporary or permanently in the database 1140. In some embodiments, the database 1140 may be integrated with the monitoring device 1150.

For instance, the system 1000 may further comprise a loudspeaker controller 1151 that may be configured to control the loudspeaker 108. For instance, the processor 1130, after processing the audio data and calculating the heart rate and respiration rate, may be further configured to send audio data to the loudspeaker 108, such audio data may then be reproduced for the user.

In some embodiments, the feedback to be sent to the loudspeaker 108 may be determined by the processor 1130 and/or monitoring device 1150 based on the determined heart and/or respiratory rates.

For instance, the audio recorder 1120, the database 1140, the processor 1130, the loudspeaker controller 1151 may be part of the processing device 1135. It should be understood that the audio recorder 1120, the database 1140, the processor 1130, and/or the loudspeaker controller 1151 may be connected wirelessly or via wires. The said components may also communicate with each other via a network (such as, for instance, internet and/or intranet).

For instance, the collected heart rate and breathing rates for a particular user may be further analysed in order to dynamically (in the real time) adjust the method of measurement and determination of the heart rate and breathing rate for that particular user. The method may also be dynamically (in the real time) adjusted based on measurements of the heart rate and breathing rate of a certain number of different users. The monitoring device 1150 may thus send feedback to the processor 1130.

Figure 16:
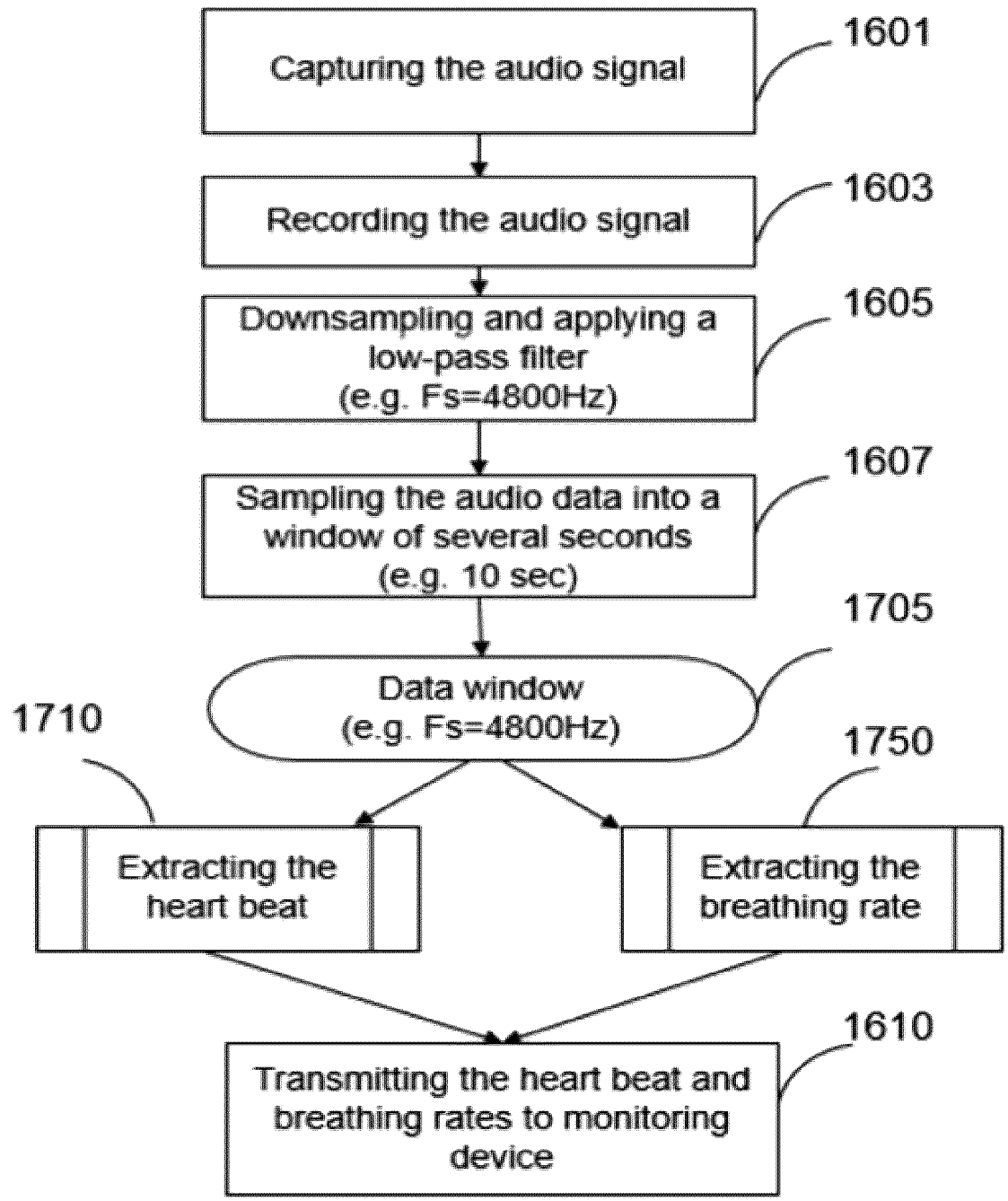
FIG. 16 shows a schematic diagram of an embodiment of the method for measurement of heart and breathing rates.

FIG. 16 shows a schematic diagram of an embodiment of the method for measurement of heart and breathing rates.

Typically, the audio data recorded has a sampling rate of 48,000 Hz. At step 1605, the data may be downsampled by, for instance, a factor of 10 to reduce processing time by applying a low-pass filter and removing samples to reduce the sampling rate. For instance, at step 1605, the data may be downsampled from 48,000 Hz to 4,800 Hz. For instance, the data may be downsampled to 4,800 Hz (sampling factor Fs may be, for instance, 4,800 Hz).

At step 1607, the data (x) may be framed (separated, downsized) into smaller data frames (also referred to herein as "data windows"). For instance, each data frame may have 10 seconds of audio data recorded.

For instance, at step 1607, the input data x may be framed into windows of 10 seconds x(n), where n may range from 0 to M−1 (for instance, M may be between 35000 and 50000).

Two processes may then be simultaneously applied to such data windows: a heart rate extraction process 1710 and a breathing rate extraction process 1750. It should be understood that although these processes may be performed consecutively, simultaneously determining the heart rate and the breathing rate may permit using this method in a real-time analysis of the condition of the user (wearer of the earpiece).

The heart rate extraction process 1710 and breathing rate extraction process 1750 may be similar in a way that the same steps may be applied to the data, although the downsampling rates and the frequencies are different.

Figure 17A:
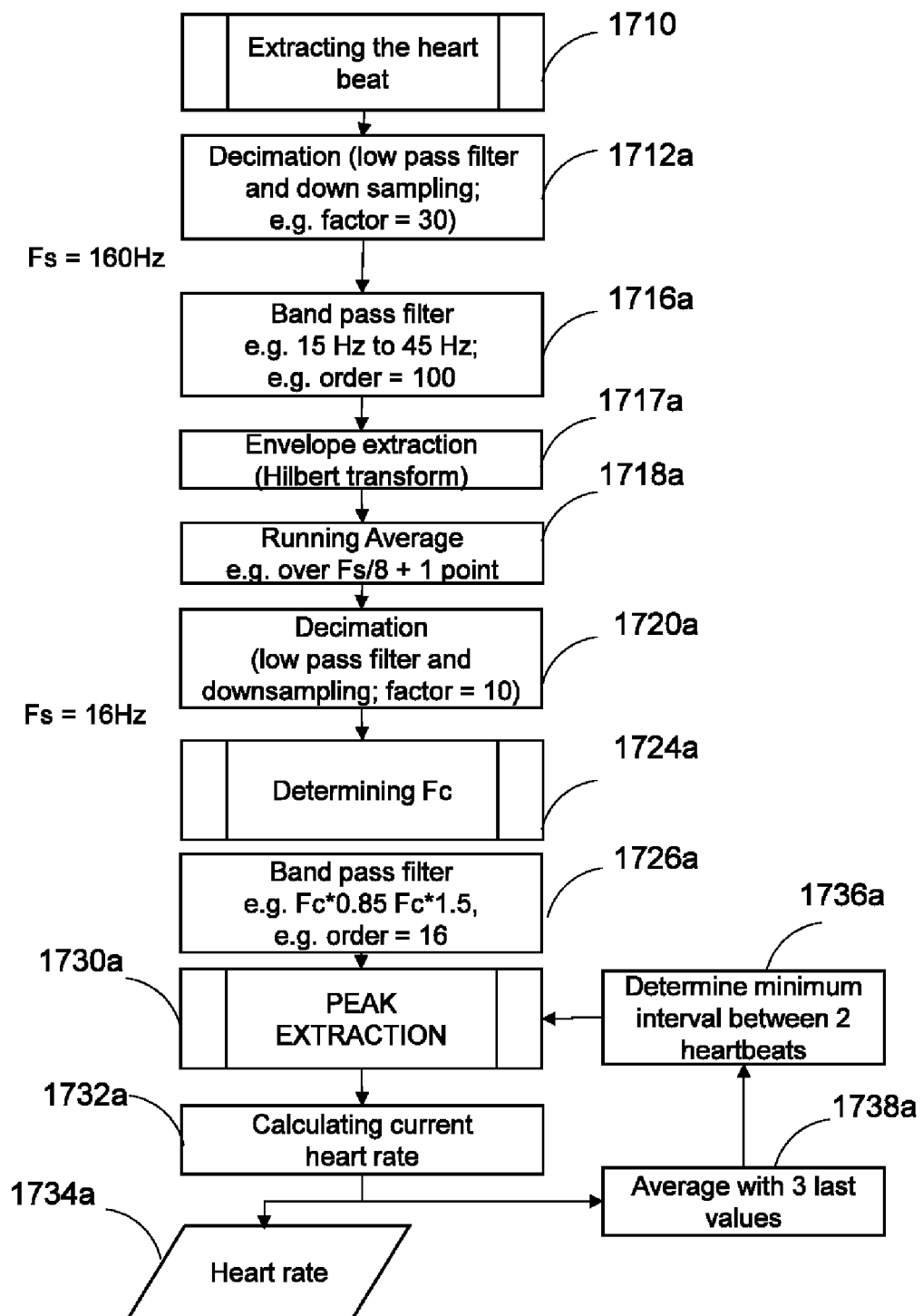
FIG. 17A shows a schematic diagram of an embodiment of the heart rate extraction process.

An embodiment of the heart rate extraction process (method) 1710 is shown at FIG. 17A. For heart rate extraction, the data x(n) may be first downsampled, for instance, by a factor of 20 to 40 in order to obtain the data frequency of between 150 and 200 Hz (e.g. 160 Hz). Such downsampling may reduce computing time and increase battery life. In some embodiments, Fs may be two times higher than the highest frequency of the band pass filter applicable at step 1716a or 1716b, respectively.

The downsampled data may then pass through the band-pass filter at step 1716a. For instance, the band-pass filter may be any known in the art finite-impulse response (FIR) filter. In some embodiments, the band-pass filter applied to the data may be less than 70 Hz. For instance, the frequency range of the band-pass filter applied at step 1716a may be between 10 Hz and 70 Hz, or between 15 Hz and 60 Hz, or between 15 Hz and 45 Hz.

In some embodiments, the frequency range of the band-pass filter applied at step 1716a may be adjusted to a particular wearer or a particular earpiece. For instance, the method 1710 and the system 1000 may thus be personalized to capture the specific characteristics of the earpiece frequency attenuation and the specific spectrum of the biosignals of the wearer. This characterization may be performed offline, in a training or initialization phase.

The downsampled data may pass through the band-pass filter at step 1716a to obtain heart rate data c (n), where n is the number of data of points. In yet other embodiments, the frequency band corresponds to the frequency band of the sounds correlated to heartbeats in the ear-canal.

Figure 17B:
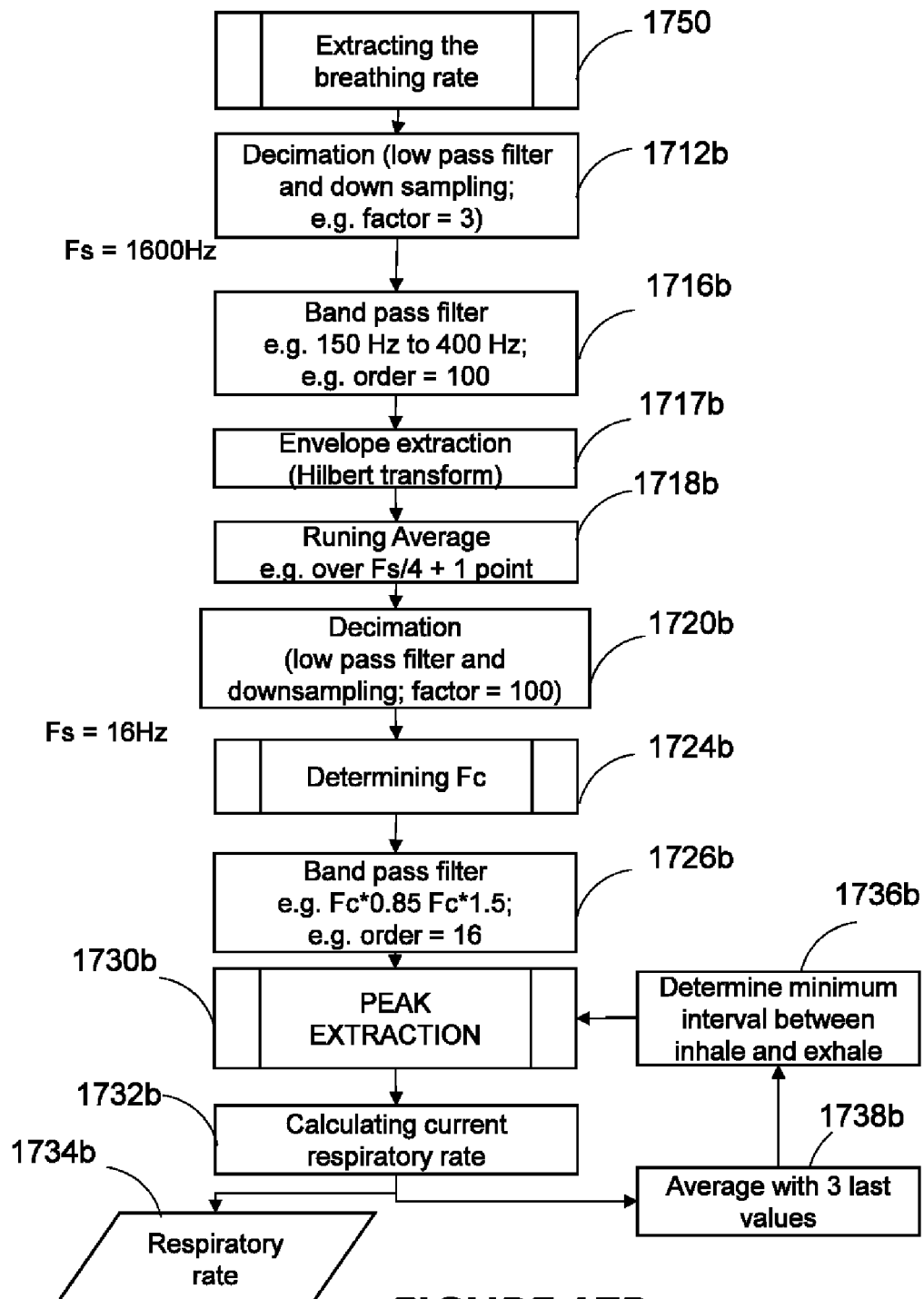
FIG. 17B shows a schematic diagram of an embodiment of the breathing rate extraction process.

An embodiment of the breathing rate extraction algorithm 1750 is shown at FIG. 17B. For breathing rate extraction, the data x(n) may be downsampled, for instance, to 1600 Hz, at step 1712b, then passed through a band-pass filter at step 1716b, to obtain breath rate data r (n). The band-pass filter applied at step 1716*b* may be a FIR filter. For instance, the frequency range of such filter may be, for instance, between 100 Hz and 600 Hz. For instance, the frequency range of the band-pass filter applied at step 1716*b* may be between, 150 Hz to 400 Hz.

Further, at steps 1718*a* and 1718*b* respectively, Hilbert Transform with a moving average may be applied to the heart rate and breath rate data c (n), r (n).

Each envelope may then be downsampled, for instance, to 16 Hz, to obtain c' (n) and r' (n) at steps 1720*a* and 1720*b*, respectively. In some embodiments, c' (n) is the envelope signal of c'(n), while r' (n) here is the envelope signal of r (n). The sampling rate may be, for instance, between 5 Hz and 20 Hz.

For instance, 16 Hz may be a suitable sampling rate to determine heart rate and breathing rate, which may correspond approximately to a signal with a maximum frequency of 7-8 Hz (approximately 400 beats per minute or cycles per minute). Such an embodiment may be used to cover a wide range of values of heart rates and breathing rates. In some embodiments, further downsampling may not provide a noticeable reduction of processing time.

Now referring to steps 1724*a* and 1724*b*, a fundamental (central) frequency (Fc) of the signal may be determined by performing a script or a procedure. At step 1726*a*, 1726*b*, the band pass filter may be applied and the determined central frequency may be used as the center frequency of the band pass filter. Steps 1724*a*, 1726 may thus provide a filtered signal.

For instance, a frequency range of the band pass filter applied at step 1726*a*, 1726*b*, may be adjusted to a particular user of the earpiece 100. For instance, the processor 1130 may adjust (e.g. dynamically, during monitoring of the user) such frequency range based on the heart rate and respiratory rate determined and collected earlier for that particular user.

In some embodiments, the steps 1712*a*, 1712*b*, 1720*a*, 1720*b* may be omitted or adjusted depending on the processing power available.

Figure 18:
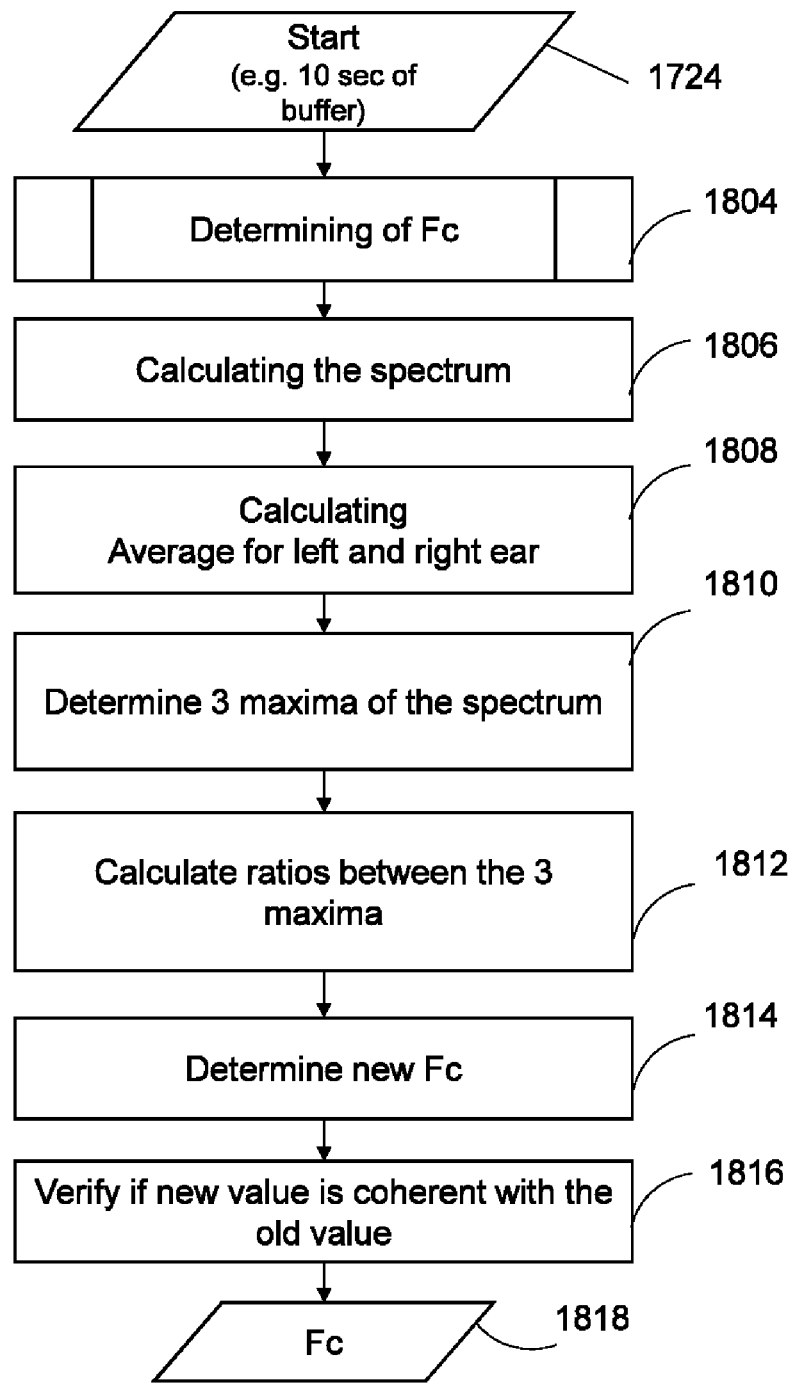
FIG. 18 shows a schematic diagram of an embodiment of determining of center frequency of the band-pass filter (Fc)

FIG. 18 shows a schematic diagram of an embodiment of determining of center frequency of the band-pass filter (Fc). The method to determine a center frequency of the band-pass filter (Fc) 1804 comprises using a filtered signal 1724. As such, the filtered signal 1724 may be buffered for a predetermined period of time, such as 10 seconds. The method 1804 may further comprise calculating the spectrum of the filtered signal 1806 and may comprise calculating an average between filtered signals from left and right ears 1808. The method 1804 may further comprise determining maxima of the spectrum 1810, such as calculating three (3) maxima of the spectrum. Based on such calculated maxima 1810, the method further comprises calculating ratios between the said calculated maxima 1812. The new calculated center frequency of the band-pass filter (Fc) is then determined 1814. The method may comprise verifying if the calculated value of the center frequency is coherent with the old value 1816. The band-pass filter (Fc) is then configured with the calculated center frequency 1818. The maxima may be harmonics of the fundamental frequency of the heartbeats (HB) and breathing cycles (BC) signals to be isolated. As such, the ratio between the maxima may allow to estimate the location of the fundamental frequency of the signal and tune the center frequency of the band-pass filter (Fc) to encompass the said fundamental frequency.

Figure 19:
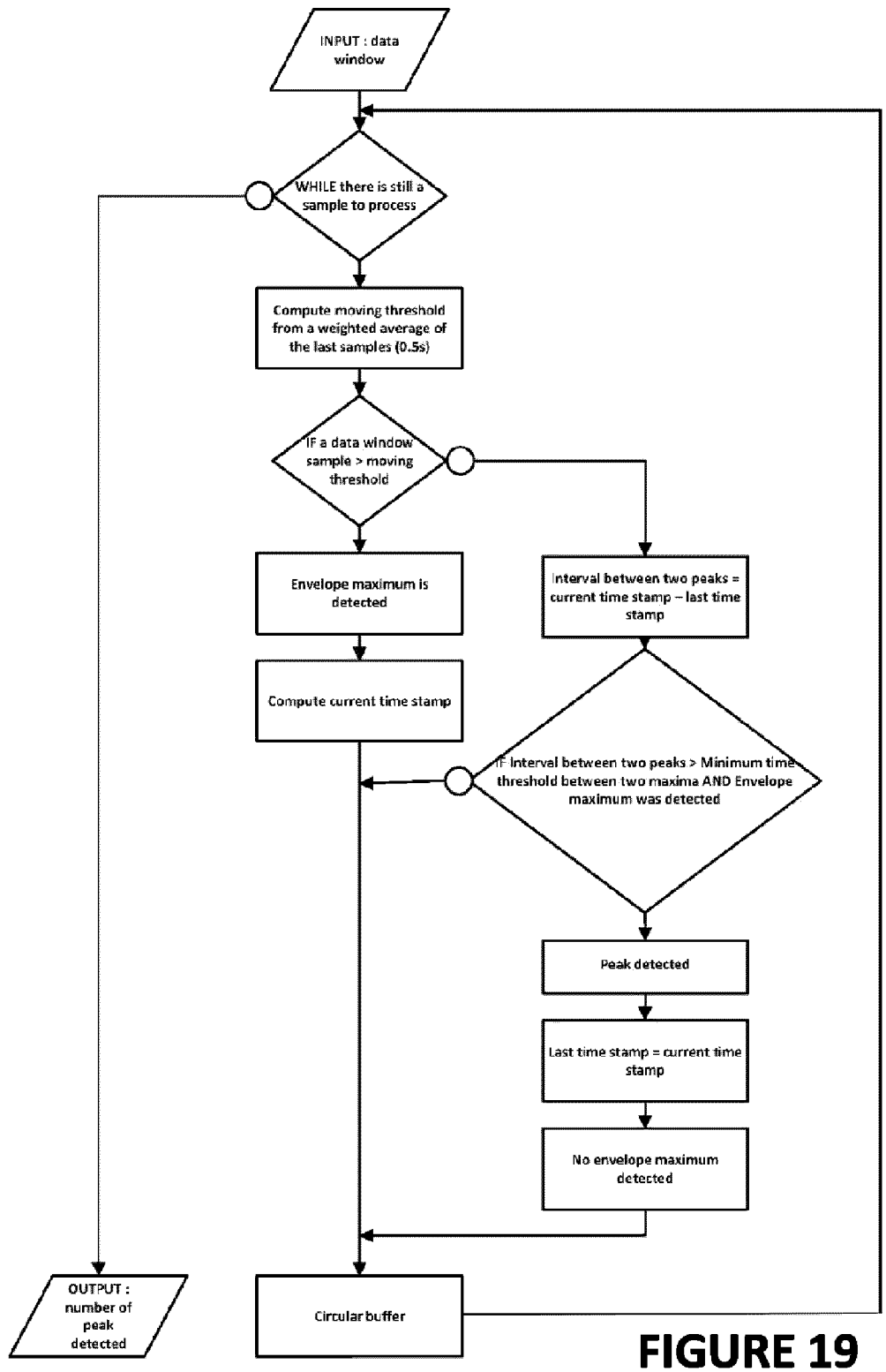
FIG. 19 shows a schematic diagram of an embodiment of determining peaks of the data, in accordance with at least one embodiment.

An embodiment of the peak extraction process applied at steps 1730*a*, 1730*b* is shown at FIG. 19. One of the steps of the peak extraction process may be applying a band-pass filter with cut-off frequencies computed from the spectra of c' (n) and r' (n) in order to obtain C (n) and R (n). Moving thresholds may then be applied to data C (n) and R (n) to determine whether a beat or a respiration phase (inhalation or exhalation) was detected. It should be understood that other methods of peak extraction may be applied to the heart rate data and breath rate data.

In some embodiments, the peak extraction applied at steps 1730*a*, 1730*b* may be adjustable to a particular user.

Heart and breathing rates may be computed based on the number of heartbeats (HB) and breathing cycles (BC) detected. A minimum sample number between two detections may be computed using previous values of the heart and breathing rates to avoid erroneous detection, assuming that these biosignals are somewhat stable over a couple of seconds.

Figure 5:
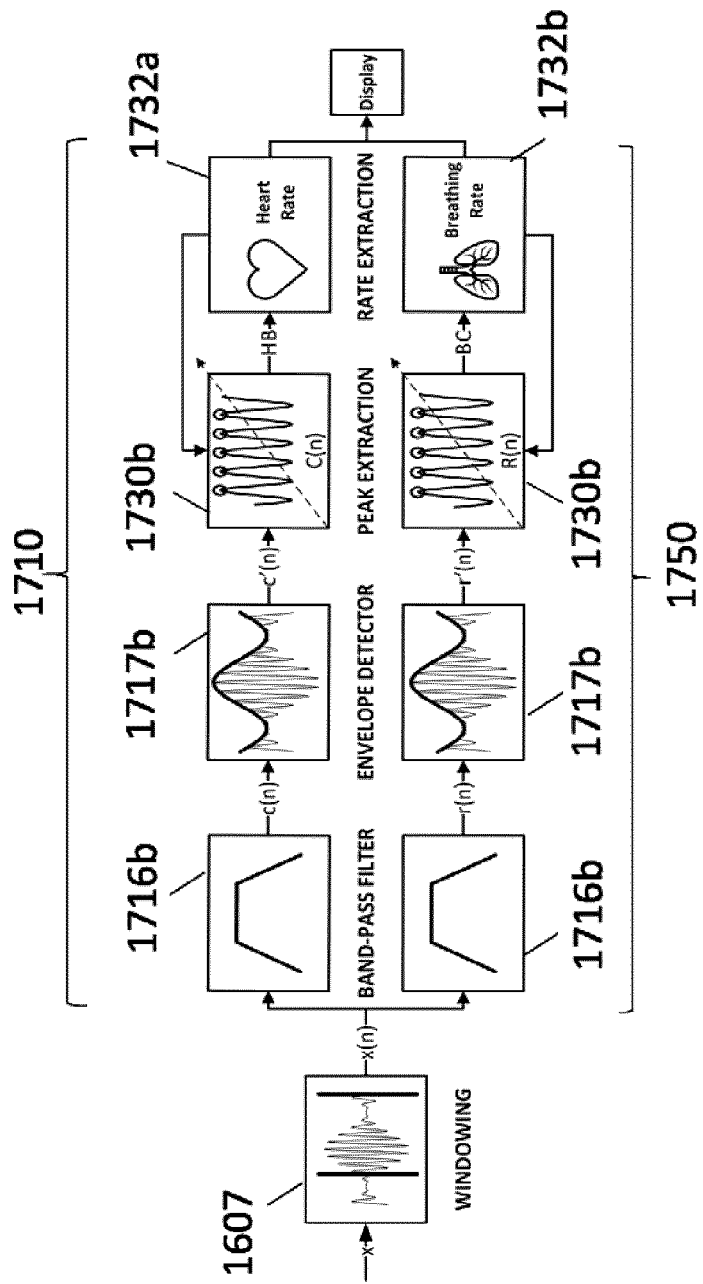
FIG. 5 shows a block diagram of the heart and breathing rate extraction algorithms, in accordance with at least one embodiment.

Referring now to FIG. 5, shown therein is a block diagram of the heart and breathing rate extraction methods. It should be noted that these methods are of low complexity and may be applied quickly to the measured data thus permitting updating and displaying the changes in the heart and breath rate on a timely basis. Low complexity of the methods reduces computing time and battery consumption.

The methods of the extraction the heart rate and breath rate may be applied even when the environment is noisy.

For instance, the denoising may be performed with a method of adaptive filtering that is adapted for biosignals such as described in U.S. Provisional Patent application Ser. No. 62/332,861, content of which is incorporated herein by reference. To adjust the adaptive filter for biosignals, a greater relative weight of the filter coefficient within the Normalize Least Mean Square (nLMS) adaptive filter may be used for the lower frequencies. Lower frequencies represent a frequency range that more closely match the frequencies of biosignals.

Figure 6:
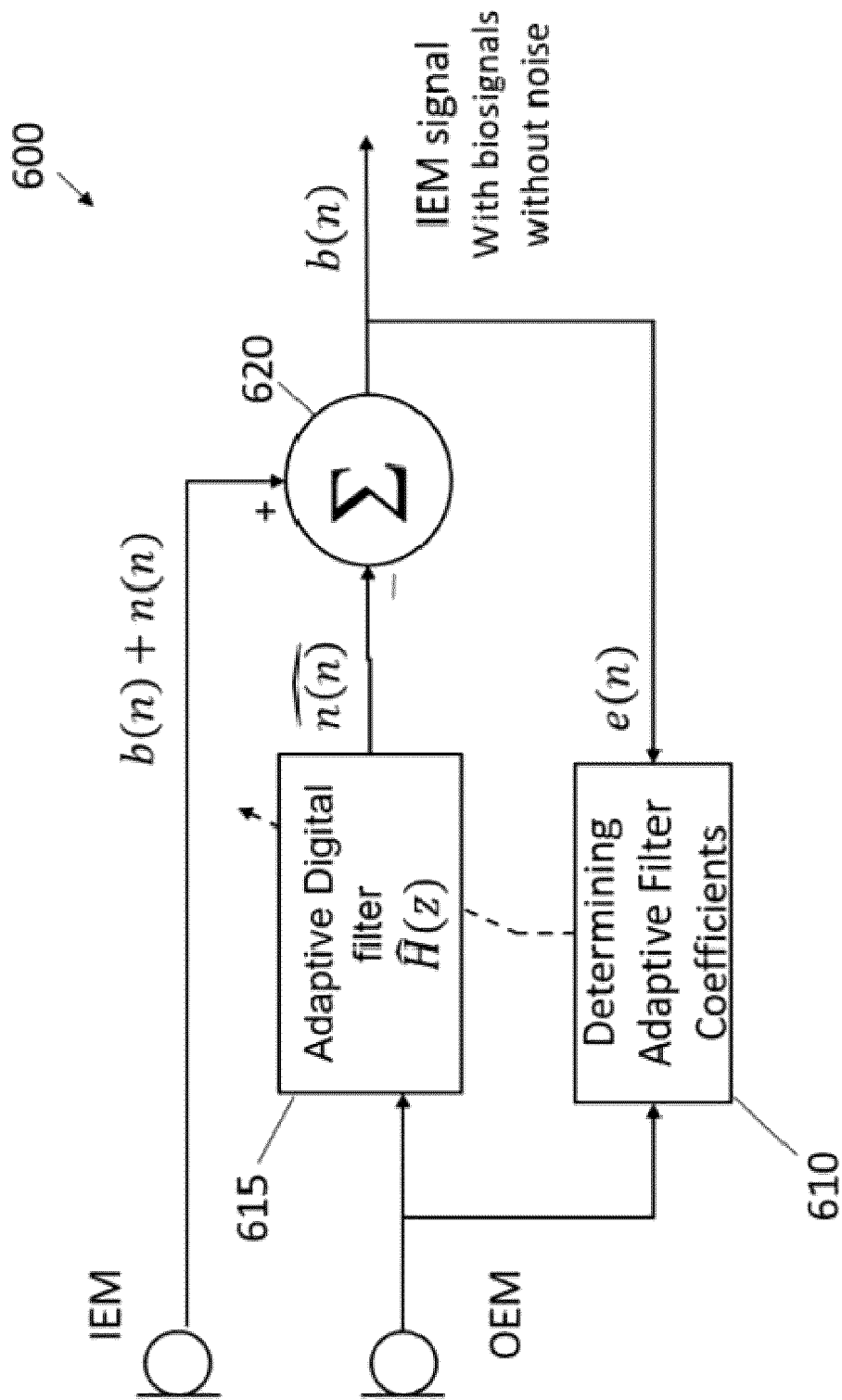
FIG. 6 shows a block diagram of denoising using adaptive filtering, in accordance with at least one embodiment.

FIG. 6 shows a block diagram of denoising 600 of the captured in-ear sound data (to remove the noise) using adaptive filtering.

For instance, the denoising 600 may be performed using a normalized least mean squared (nLMS) adaptive filter. In such adaptive filter, the signal of interest may be the error signal e (n). For instance, the denoising 600 may comprise determining the noise to be removed from the in-ear signal (estimated residual noise).

The denoising 600 of captured in-ear sound data may comprise the following steps. First, parameters of an adaptive filter 610 may be determined using the error data e (n) and the outer-ear sound data. The adaptive filter 615 may be then applied to the outer-ear sound data to obtain filtered outer-ear sound data n (n). The filtered outer-ear sound data may then be subtracted from the in-ear sound data at step 610 to obtain the in-ear sound data without noise (b (n)). The parameters of the adaptive filter may be adjustable as a function of output of 620.

At FIG. 6, $\widehat{H(z)}$ is the estimated transfer function of the earpiece (primary transfer function) and $\widehat{n(n)}$ is the estimated residual noise.

The heart rate and breathing rate extraction algorithms 1710, 1750 as described herein may then be applied to denoised biosignals.

Figure 21:
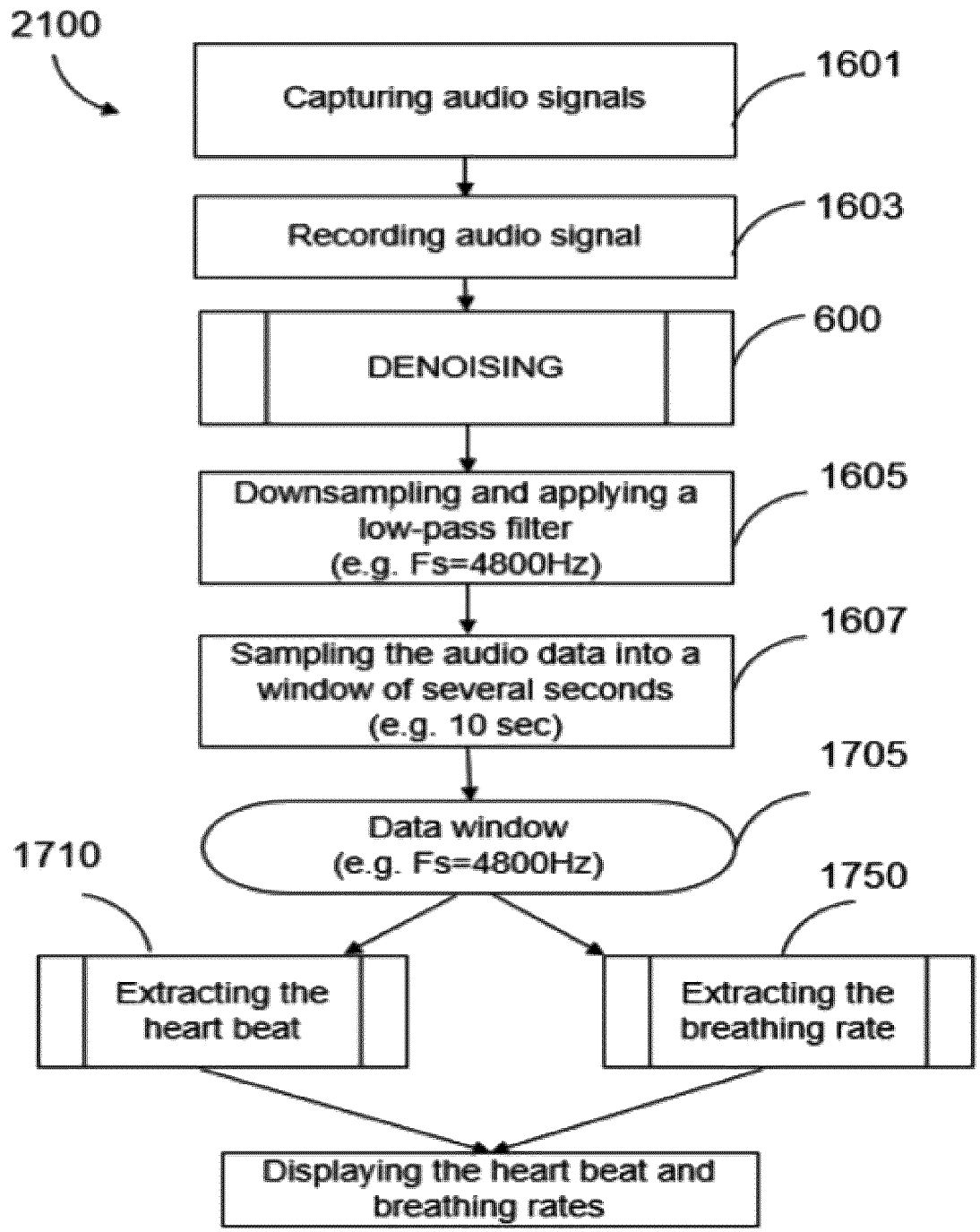
FIG. 21 shows a schematic diagram of an embodiment of the method for measurement of heart and breathing rates with denoising, in accordance with at least one embodiment.

FIG. 21 shows an embodiment of the method 2100 for measurement of heart and breathing rates with a denoising step 600.

Experiment

Sounds in the occluded ear canal were measured by the in-ear microphone (IEM) located in an instrumented earpiece. A database of in-ear audio recordings in the occluded ear canal was created using a sample of 25 individuals. During the experiment, subjects were asked to breathe at various rhythms and intensities through the mouth or nose to achieve realistic recordings. These real-life sounds were recorded. A total of 16 hours and 40 minutes of sounds in the ear canal were recorded.

Heart and respiration sound features were then investigated as recorded at this specific location using the method as described herein (signal processing algorithms) to assess the user's heart and breathing rates.

Results from the algorithms were then compared to the numerical values obtained by a commercial reference device used during the measurement. Finally, noise was added numerically to the IEM signal to assess the robustness of the algorithms against ambient noise for further applications, such as monitoring workers' health. The noise was added to the recorded signal and a denoising filter was applied to test the robustness of the method in noisy environments.

In the example described herein, the absolute mean error for heart and breathing rate extractions were obtained to be, respectively, 4.3 beats per minute and 3.0 cycles per minute. In this example, for noise of up to 110 dB SPL, extraction of heart rate with small errors was achieved, whereas the extraction of the breathing rate with noise was less accurate. In this example, the algorithm (especially for heart rate) has shown to have low sensitivity to simulated high noise environments.

The extraction of the heart and breathing rates from an acoustical measurement in the occluded ear canal may be performed with high environmental noise.

Data Acquisition

In this experiment, audio-signals in the left and right ears were recorded simultaneously on 25 subjects (19 males and 6 females, aged between 21 and 53, with an average of 28).

Each participant was equipped with two instrumented earpieces developed by EERS Technologies (Montreal, Canada) with disposable foam tips (Tx200, Comply, Oakdale, USA). Each earpiece had two microphones and one loudspeaker as illustrated in FIGS. 1A and 1B. The IEM was used to record sounds in the ear canal. Audio data was recorded with a multichannel digital audio recorder (H4n, Zoom Corporation, Tokyo, Japan) at a sample rate of 48 kHz. FIGS. 1A and 1B show an example of instrumented earpiece worn by each subject in each ear.

A wearable chest belt (BioHarness™ 3, Zephyr, Annapolis, USA) was used as a reference system. Typically, the BioHarness™ may provide quite accurate measurements of heartbeats and respiration when used at rest. The data acquisition framework developed by MuSAE Lab was used to record and display raw data from the BioHarness™.

A Python routine was developed to synchronize audio data and BioHarness™ data. A small delay between audio data and BioHarness™ data might have existed (no greater than 125 ms). In this example, such delay did not affect the process of extraction of the heart and breathing rates.

Experimental Protocol

To provide recordings that are as realistic as possible, the subjects were asked to breathe at various rhythms and intensities. They were seated in an audiometric double-wall sound booth during the recordings. Table 1 presents the experimental protocol, which was conducted once with nasal breathing and once with mouth breathing, resulting in ten different respiration types.

Table 1 presents an experimental protocol showing real-life recordings, done once with nasal breathing and once with mouth breathing.

TABLE 1

| Action | Acronym | Duration (seconds) |
|---|---|---|
| Deep slow Breathing | DB | 90 |
| Apnea | A1 | 20 |
| Normal Breathing | NB | 240 |
| Apnea | A2 | 20 |
| Fast Breathing | FB | 30 |
| Apnea | A3 | 20 |
| Exercise on a bike | — | 90 |
| Apnea after exercise | AE | 10 |
| Normal Breathing after Exercise | NBE | 180 |

To assess whether the subject's earpieces were well positioned within the ear canal and provided a good attenuation of the ambient noises, the transfer functions between OEM and IEM were computed for each subject's ear by playing white noise in the sound booth at 85 dB SPL: 30 seconds at the beginning and 30 seconds at the end of the recording session.

No target rhythms or expiration volumes were imposed. The subjects were free to interpret how to breathe according to the type of respiration and therefore, the obtained database contains a wide range of real-life signals. Apnea recordings were used for spectral characterization only.

Database Analysis

Five subjects were removed from the analysis, because of a synchronization issue between the audio and BioHarness™ signals. Table 2 shows information about the values of heart and breathing rates recorded for the 20 subjects.

Heart and breathing rate values were recorded with BioHarness™ a portable system allowing to log data wirelessly. Table 2 presents the average, standard deviation, minimum and maximum values across all conditions for 20 subjects. As can be noticed, a wide range of heart and breathing rates values were recorded.

TABLE 2

| | Average | Standard deviation | Minimum | Maximum |
|---|---|---|---|---|
| Heart Rate (Beats Per Minute, BPM) | 78.6 | 12.6 | 50.7 | 120.7 |
| Breathing Rate (Cycles Per Minute, CPM) | 22.8 | 10.7 | 3.3 | 138.0 |

Figure 2:
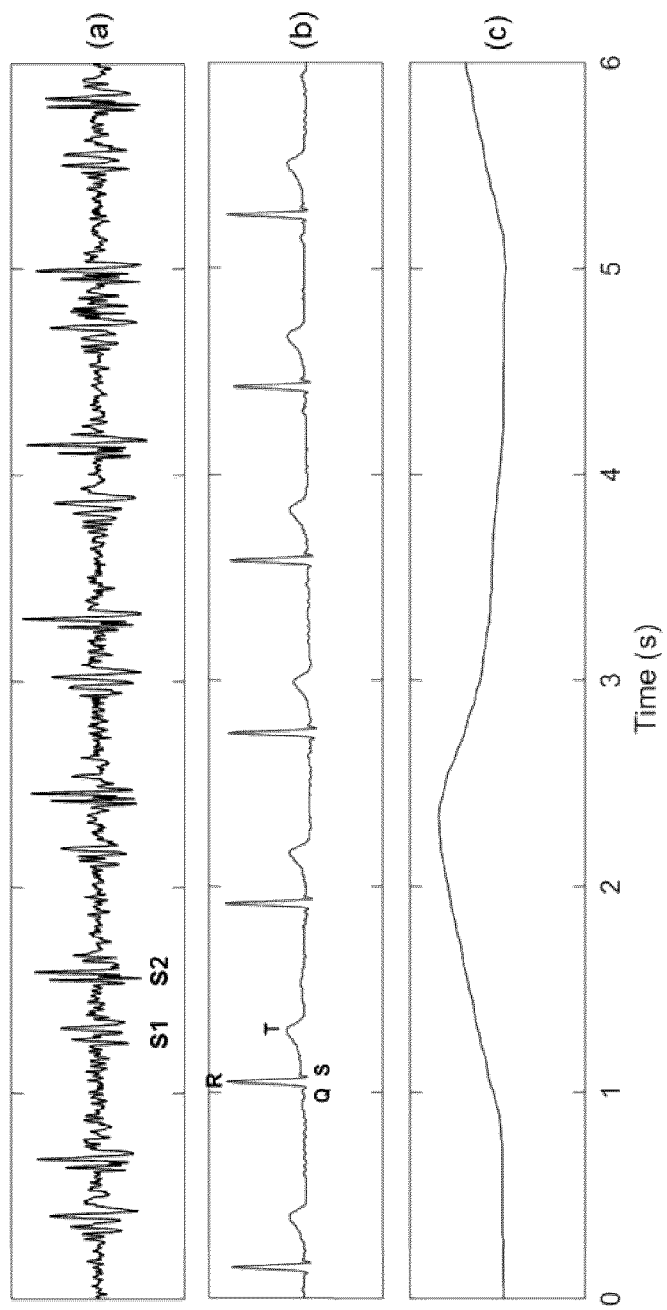
FIG. 2 shows: (a) Time signal recorded by the IEM, showing heart sounds S1 and S2; (b) heartbeat reference recorded by the BioHarness™, which is an electrocardiogram; (c) respiration reference recorded by the BioHarness™, which is a respiratory inductance plethysmography showing inhaling (ascending phase) and exhalation (descending phase)

An illustrative recording of sound with normal breathing in the occluded ear canal is shown in FIG. 2 (a) with the BioHarness™ reference signals in FIG. 2 (b) and FIG. 2 (c). In particular, FIG. 2 shows: (a) Time signal recorded by the IEM, showing S1 and S2. (b) Heartbeat reference recorded by the BioHarness™, which is an electrocardiogram. (c) Respiration reference recorded by the BioHarness™, which is a respiratory inductance plethysmography showing inhalation (ascending phase) and exhalation (descending phase).

If the respiration is shallow, it may be almost non-measurable by the IEM. When breathing is stronger, the microphone may measure respiration sounds.

The two major heart sounds (S1 and S2) are clearly discernible. S1 corresponds to the closure of the tricuspid and mitral valves and occurs after the RS segment of an ECG signal. S2 corresponds to the closure of the aortic and pulmonary valves and occurs during the T wave of an ECG signal. The respiration sounds result from turbulence in nasal and oral cavities and respiratory conduits. The amplitude of respiration sounds may be very small in normal respiration. If the intensity of the respiration is stronger, the respiration's sound amplitude may exceed the heart's sound amplitude.

Figure 3:
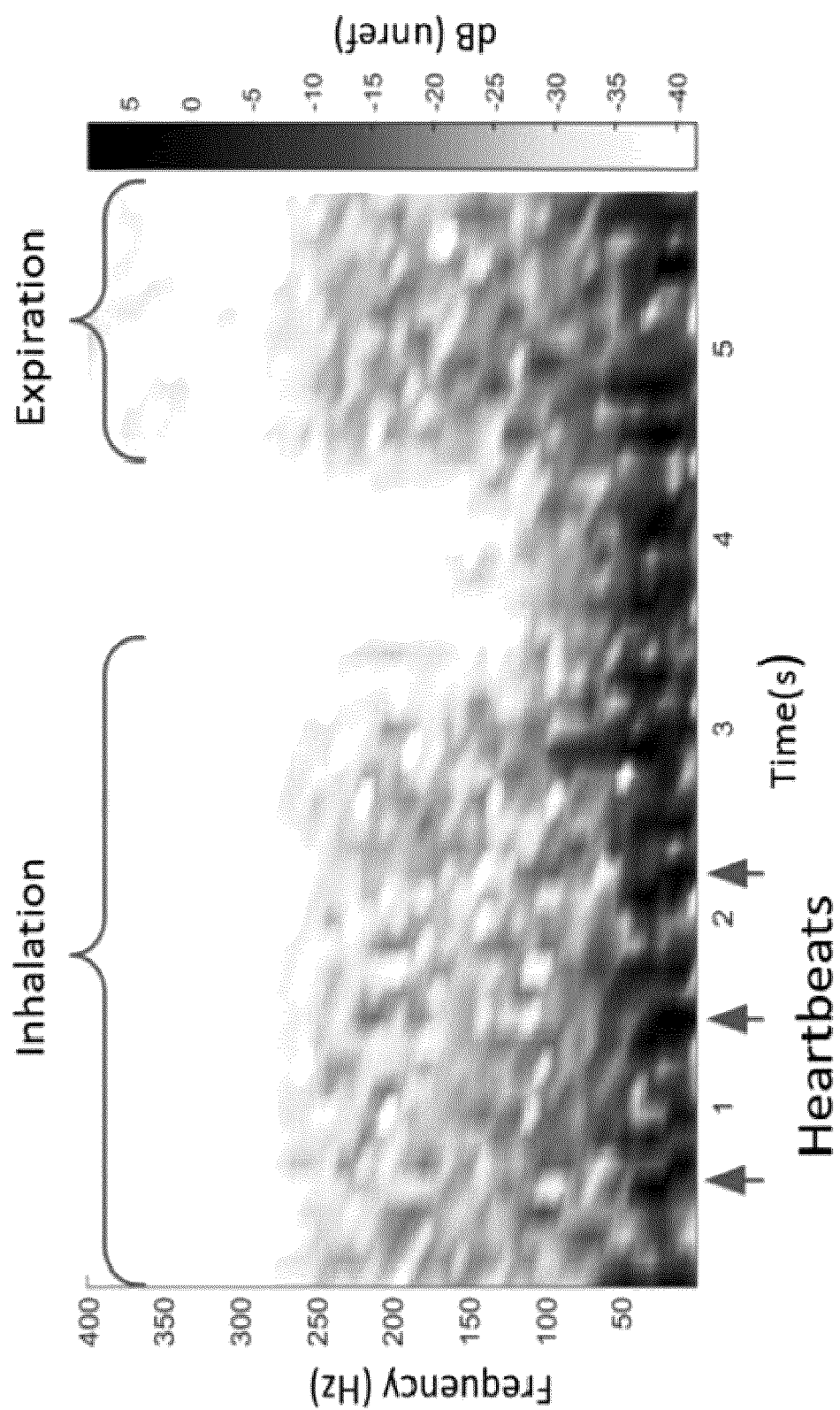
FIG. 3 shows an illustrative spectrogram of deep mouth breathing for one subject, measured with an embodiment of the method and system as described herein.

FIG. 3 shows the spectrogram of the audio signal with deep mouth-breathing for one subject. In particular, FIG. 3 shows an illustrative spectrogram of deep mouth breathing for one subject, showing that both breathing and heartbeats may be measured with the IEM. At FIG. 3, the inhalation is followed by a short pause and then an expiration. Heart sounds are identified by black spots below 60 Hz. The end of an inhalation phase is shown, followed by a short pause and then expiration. Physiological noise at frequencies below 150 Hz was observable due to shell activity (muscle activity, blood flow, etc.).

Figure 4:
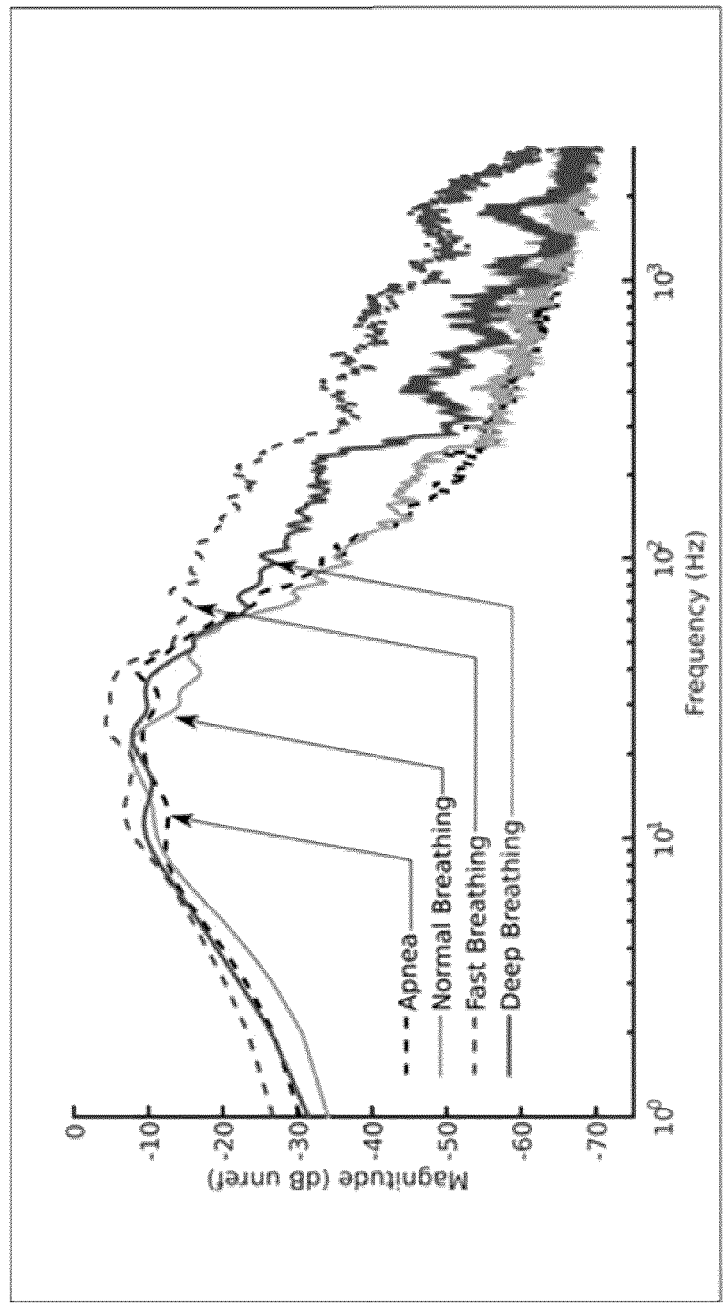
FIG. 4 shows measured spectra of four types of nose respiration for one subject, showing different spectral characteristics to distinguish respiration types.

Illustrative spectra of four types of respiration (apnea, normal breathing, fast breathing, and deep breathing) are shown in FIG. 4 for one subject. The energy of heart sounds was maximized in the frequency band between 10 to 50 Hz. Respiration sounds appear to have low frequency components in the same band as heart sounds. In this example, the energy in the band of 100 to 400 Hz varied greatly depending on the subject and type of respiration.

Respiration sound energy drops when frequency increases and sounds above 3000 Hz are not audible. Moreover, when respiration was light, such as in normal respiration, sounds were almost non-measurable by the IEM (FIG. 2 (a)).

Sound pressure levels inside the ear canal may range between 45 dB and 65 dB, or between 20 dBA to 40 dBA when using A-weighting filters, because of low frequency components.

Lookup Dictionary

Figure 15C:
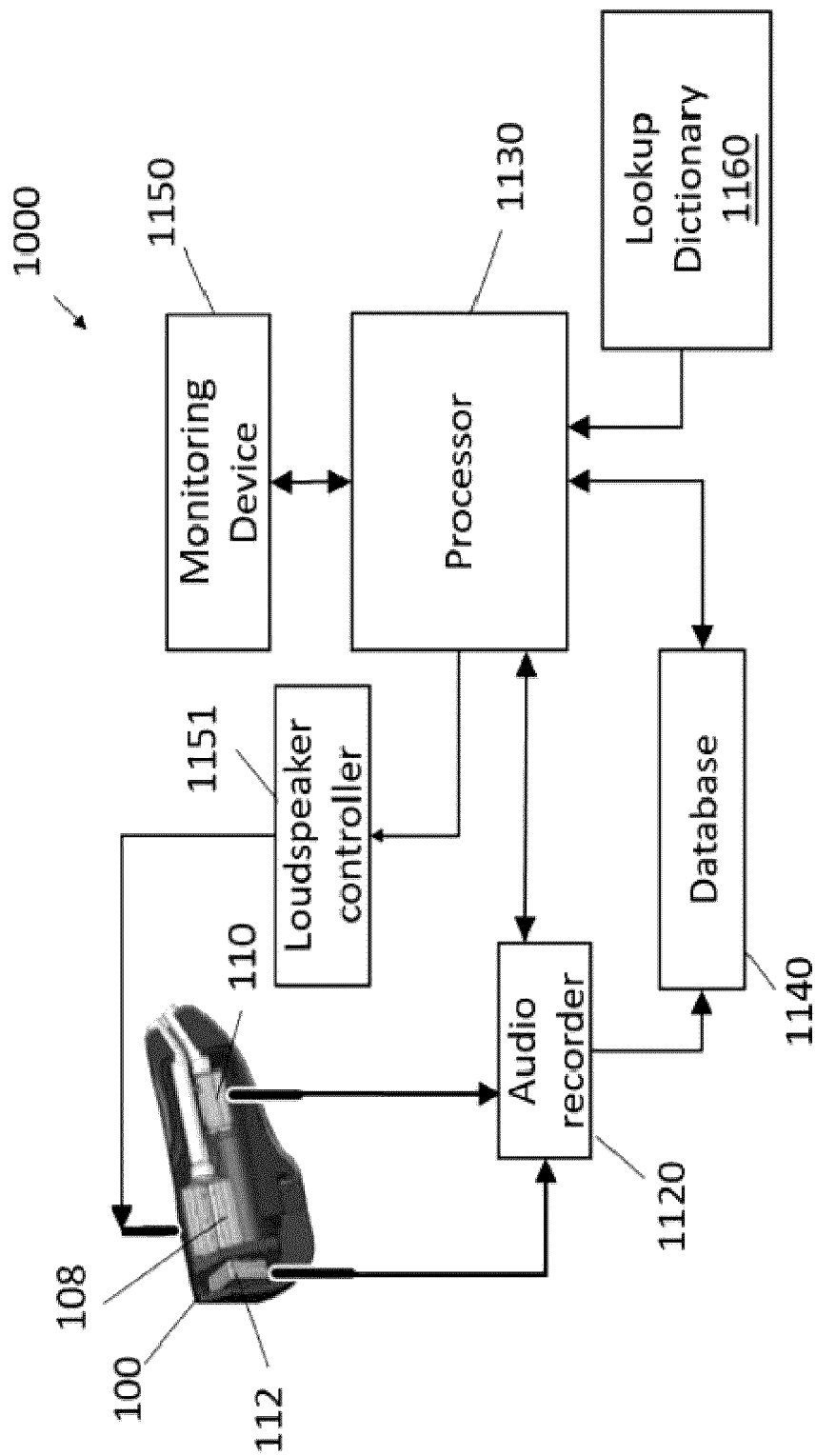
FIG. 15C shows the system for measurement of heart and breathing rates, in accordance with at least one embodiment.

According to some embodiments, the system 1000 comprises a lookup dictionary 1160, as presented in FIG. 15C. The lookup dictionary 1160 is a database that contains various heart beat and respiratory rate samples that have been previously recorded, analyzed and associated to a at least one attribute. The lookup dictionary 1160 contains various predetermined sample-attribute associations or various (sample range)-attribute associations. In some embodiments, the samples are associated to one or a variety of attributes such as a source type attribute, a physiological state attribute, an emotional state attribute, etc. It shall be recognized that a single sample can be associated to a combination of attributes. For instance, the source type can indicate vascular system source (e.g. a heartbeat source) or respiratory system source. The physiological state attribute can represent various health indicators, for instance a health indicator can be represented as one of three health levels, either a good health level, an average health level or a poor health level. Notice that any number of health indicator levels are possible, depending on the required precision. The emotional state attribute can represent various emotions, such as an anxious state, a calm state, a tired state, a happy state, etc. It shall be recognized that the attributes can be determined according to a user's personal data such as age, gender, weight and height, According to some embodiments, the processing device 1130 is adapted or configured to access the lookup dictionary 1160, compare the captured in-ear audio signal to the various samples or sample ranges of the lookup dictionary 1160 and determine at least one associated attribute. It shall be recognized that the processor may be configured or adapted to compare the captured in-ear audio signal to samples or sample ranges of the lookup dictionary 1160 according to a user's personal data (e.g. age, gender, weight and height).

According to some embodiments, the processor 1130 is configured to send the determined attributes to the monitoring device 1150.

According to another embodiment, the processor 1130 is further configured to analyze the determined attributes and provide a general state indicator. The general state indicator can be a health state indicator, an emotional state indicator, an activity type state indicator, etc. or any combination thereof. Notice that the general state indicator may be provided following an analysis of attributes determined according to a given period of time or according to a previous general state indicator. For instance, a general health indicator may be an average of the health indicators associated to samples that are comparable to the in-ear signals collected during a given period of time such as twenty-four hours. In another case, a general state indicator may be provided according to various emotional states identified according to the in-ear signals collected during a given period of time such as an hour or according to the in-ear signals collected during a given period of time and a previous general state indicator. For instance, a current general state indicator identified as "happy" could only be possible if the previous general state indicator was "excited" or "calm". A "sad" previous general state indicator could not be followed by a current general state indicator that is "happy".

According to yet another embodiment, the general state indicator is determined according to various combination of types of attributes such as a health indicators and emotional indicators. Moreover, the general indicators can be correlated with another detected signal that has been captured by another biosensor or by the in-ear sensor.

It shall be recognized that the lookup dictionary 1160 can be replaced by any other type of data source or data storage unit. Moreover, the lookup dictionary 1160 can be replaced by an algorithm that is executed. by the processor 1130. The algorithm can be a machine learning algorithm trained according to the content of a data source having predetermined sample-attribute associations or (sample range)-attribute associations. In some embodiments, the algorithm is loadable in a memory module of the system 1000 and the memory module is accessible by the processor 1130.

Figure 22A:
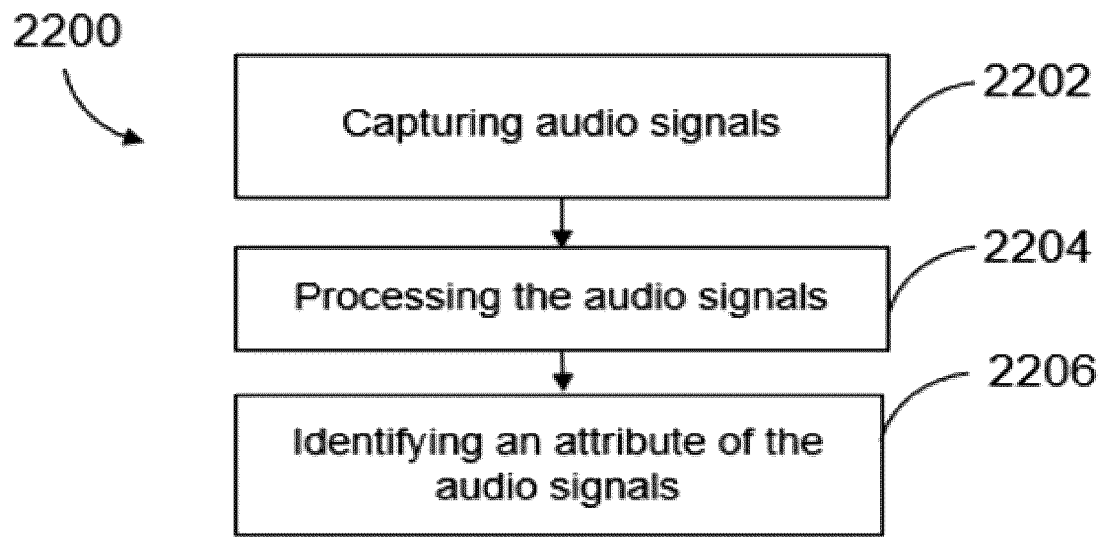
FIG. 22A shows a schematic diagram of an embodiment of the method for measurement of heart or breathing rates by determining an attribute, in accordance with at least one embodiment.

Presented in FIG. 22A is a method 2200 for determining an attribute of the in-ear audio signal, according to one embodiment. The method 2200 comprises capturing 2202 the in-ear audio signal inside an ear canal of a user with an in-ear microphone. Then processing 2204 the in-ear audio signal and identifying 2206 an attribute of the in-ear audio signal according to a predetermined audio signal association. The attribute is associated either one of both of a heart rate and a breathing rate.

Figure 22B:
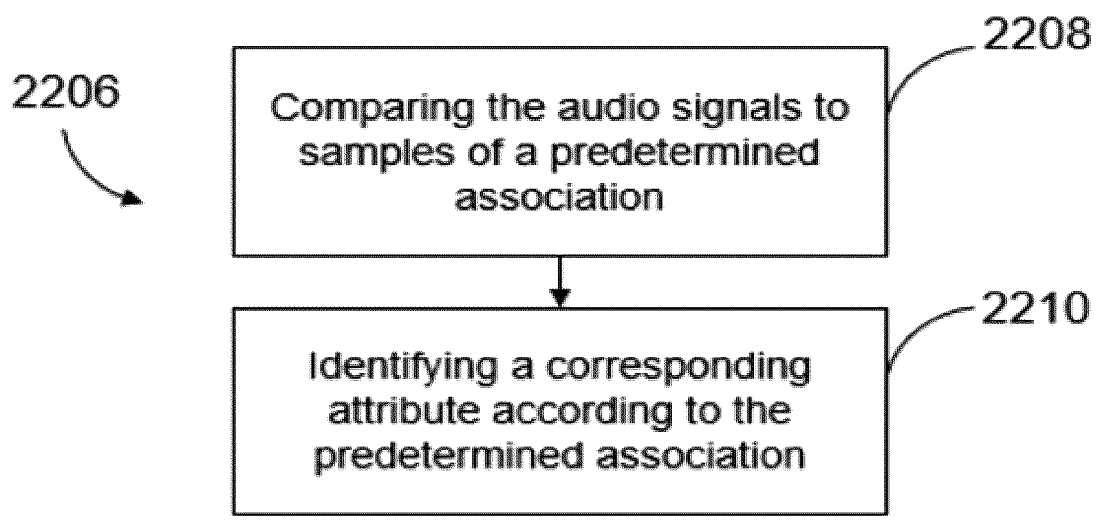
FIG. 22B shows a schematic diagram of determining an attribute according to a predetermined association, in accordance with at least one embodiment.

Presented in FIG. 22B is a method of identifying 2206 an attribute of the in-ear audio signal. The method 2206 comprises comparing 2208 the in-ear audio signal to samples of a predetermined association. If a match is found the method 2206 identifies 2210 a corresponding attribute. It shall be recognized that the comparing 2208 can be performed according to a predetermined allowable error margin. Moreover, the comparing may further comprise comparing the in-ear audio signal to a range of samples.

It shall further be understood that the in-ear audio signal may further comprise a plurality of in-ear audio signals and that a desired one or group of in-ear audio signals are extracted during the processing 2204. Moreover, the method

2200 for determining an attribute of the in-ear audio signal can include extracting in-ear audio signals according to the methods described herein.

Methods

Signal processing algorithms and methods as described herein were used to extract heart and breathing rates. To simulate a real-life situation, the audio recordings were sequentially added in this specific order: mouth breathing (normal, fast, normal after exercise, deep slow) then nasal breathing (normal, fast, normal after exercise, deep slow). A total of 36 minutes per subject with 8 respiration types were analyzed (for both ears).

Algorithms and Methods for Extracting Heart and Breathing Rates

A block diagram of an embodiment of the method for extracting heart and breathing rates is shown in FIGS. 5 and 16-19.

In this example, first, recorded signals were downsampled to 4800 Hz to reduce processing time, by applying a low-pass filter and removing samples to reduce the sampling rate. The first stage framed the input data x into windows of 10 seconds x(n), where n ranged from 0 to M−1 (M=47999).

For instance, such downsampling may reduce computing time and lower battery consumption of the devices of the system 1000.

Then, the signal was sent to two similar processes: one for heart rate extraction 1710, one for breathing rate extraction 1750.

For heart rate extraction, the window data x(n) was downsampled to 160 Hz, then band-pass filtered from 15 Hz to 45 Hz, to obtain c (n). For breathing rate extraction, the window data x(n) was downsampled to 1600 Hz, then band-pass filtered from 150 Hz to 400 Hz to obtain r (n).

The Hilbert Transform with a moving average was then applied to the filtered data c (n) in order to extract an envelope. Each envelope was downsampled to 16 Hz to obtain c' (n) and r' (n), where c' (n) is the envelope signal of c (n) and r' (n) is the envelope signal of r (n). Then, the peak extraction processes 1730a, 1730b included several steps, one of which was a band-pass filter with cut-off frequencies computed from the spectra of c' (n) and r' (n) to obtain C (n) and R (n). Then, moving thresholds were applied to C (n) and R (n) to determine whether a beat or a respiration phase (inhalation or exhalation) was detected.

Heart and breathing rates were computed based on the number of heartbeats (HB) and breathing cycles (BC) detected. A minimum sample number between two detections was computed using previous values of the heart and breathing rates to avoid erroneous detection, assuming that these biosignals are somewhat stable over a couple of seconds.

To evaluate the performance of the methods, the absolute error for one subject and one sequence of 18 minutes was computed with the following formula:

$$\varepsilon = \frac{1}{N}\sum_{i=1}^{N}\left|Ref_i - A_b\right|,$$

where $Ref_i$ is the value of the reference rhythm: beats per minute (BPM) or cycles per minute (CPM). $A_i$ is the value of the rhythm computed by the algorithms (BPM or CPM) and N is the number of observations.

Heart and breathing rates were computed during 5 seconds each using the current detections of HB and BC and two previous values of the heart and breathing rates. Also, the relative error was defined by the difference in percentage between the reference values and the algorithm output values.

Denoising of Biosignals from Ambient Noise

To simulate a noisy work environment such as a mine or a factory plant, noise was added numerically to the IEM signal and the performance of the developed algorithm could then be assessed in the presence of these disturbances.

White noise and industrial noise from NASA's steam plant database were used.

Figure 20:
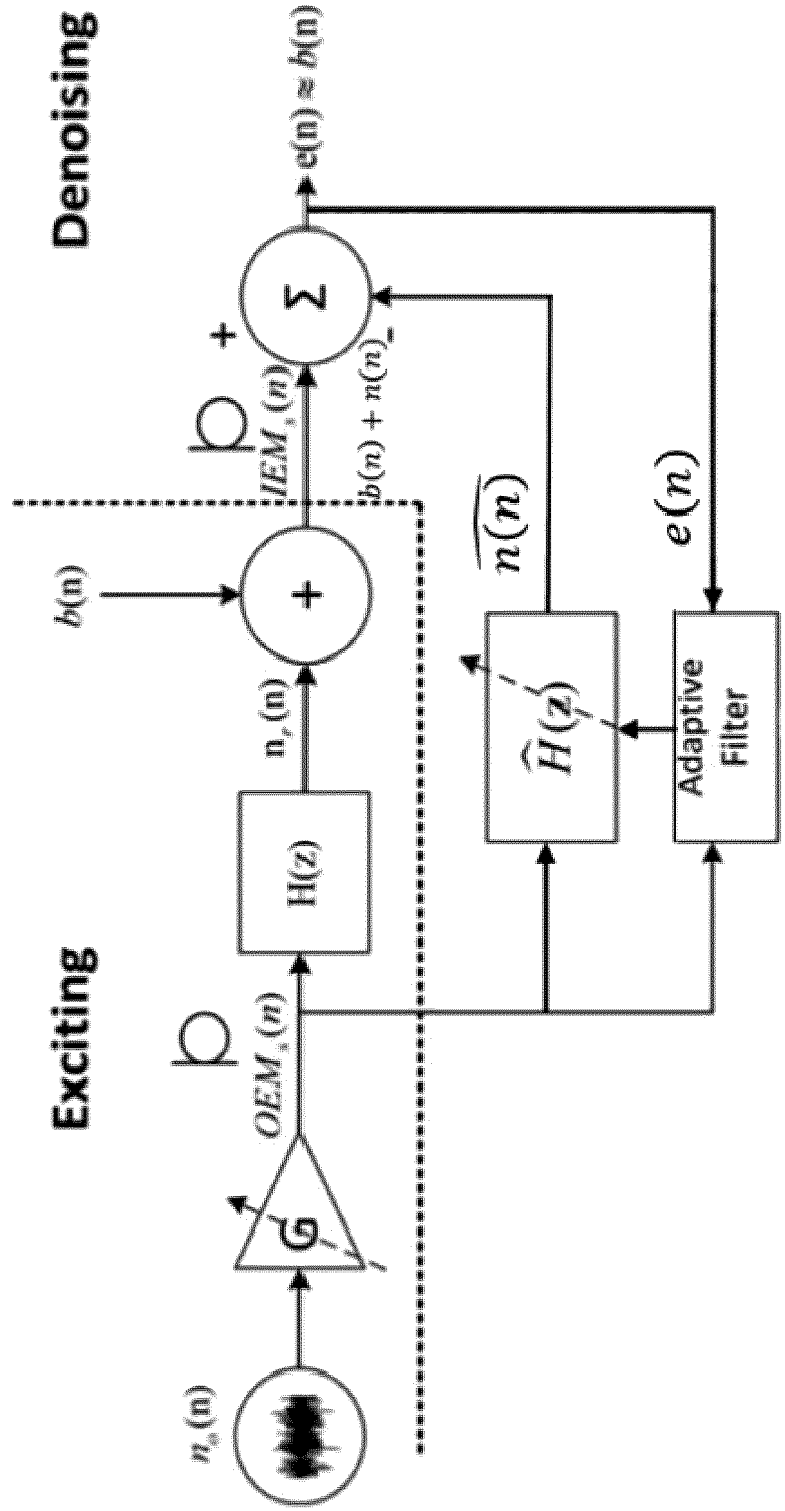
FIG. 20 shows a block diagram of denoising using adaptive filtering, in accordance with at least one embodiment.

FIG. 20 shows a block diagram of the process of exciting and then denoising that was applied to measured data.

First, the exciting part consisted of multiplying the noise signal (white or industrial noise) $n_o(n)$ by a gain G, which was computed to obtain a calibrated noise level ranging from 50 to 110 dB SPL (in steps of 5 dB). Then, the normalized noisy signal OEMs (n) went through H (z) to obtain the residual noise inside the ear $n_r(n)$. At FIG. 20, H (z) is the true transfer function of the subject's earplug computed from measurements made during the experimental protocol. Then, $n_r(n)$ was added to the biosignals b (n) measured by the IEM, which contained heart and respiration sounds, to obtain the noisy biosignals.

Second, the denoising part consisted of removing the residual noise from the noisy $IEM_s(n)$ signal originating from ambient noises and disturbances. The denoising was performed using a normalized least mean squared (nLMS) adaptive filter. Such filter was described and applied for denoising speech signals captured with an IEM in Rachel Bouserhal, Tiago Falk, and Jeremie Voix, "*In-ear microphone speech quality enhancement via adaptive filtering and artificial bandwidth extension*," The Journal of the Acoustical Society of America, vol. 141, no. 3, pp. 1321-1331 March 2017 (also referred to herein as "Bouserhal et al."). In contrast to Bouserhal et al., the adaptive filter in the present example was adapted to biosignals as described above.

In such adaptive filter the signal of interest may be the error signal e (n). The noise to be removed from the in-ear signal (estimated residual noise) was determined.

Referring to FIG. 20, $\widehat{H(z)}$ is the estimated transfer function of the earpiece (primary transfer function) and $\widehat{n(n)}$ is the estimated residual noise. The heart rate and breathing rate extraction algorithms as described herein were then applied to denoised biosignals.

Results

Results were obtained using a 36-minute long signal per subject, containing 8 respiration types. Algorithms were implemented in Matlab™.

The absolute and relative error defined above were calculated for the extraction algorithms for heart and breathing rates.

Figure 7:
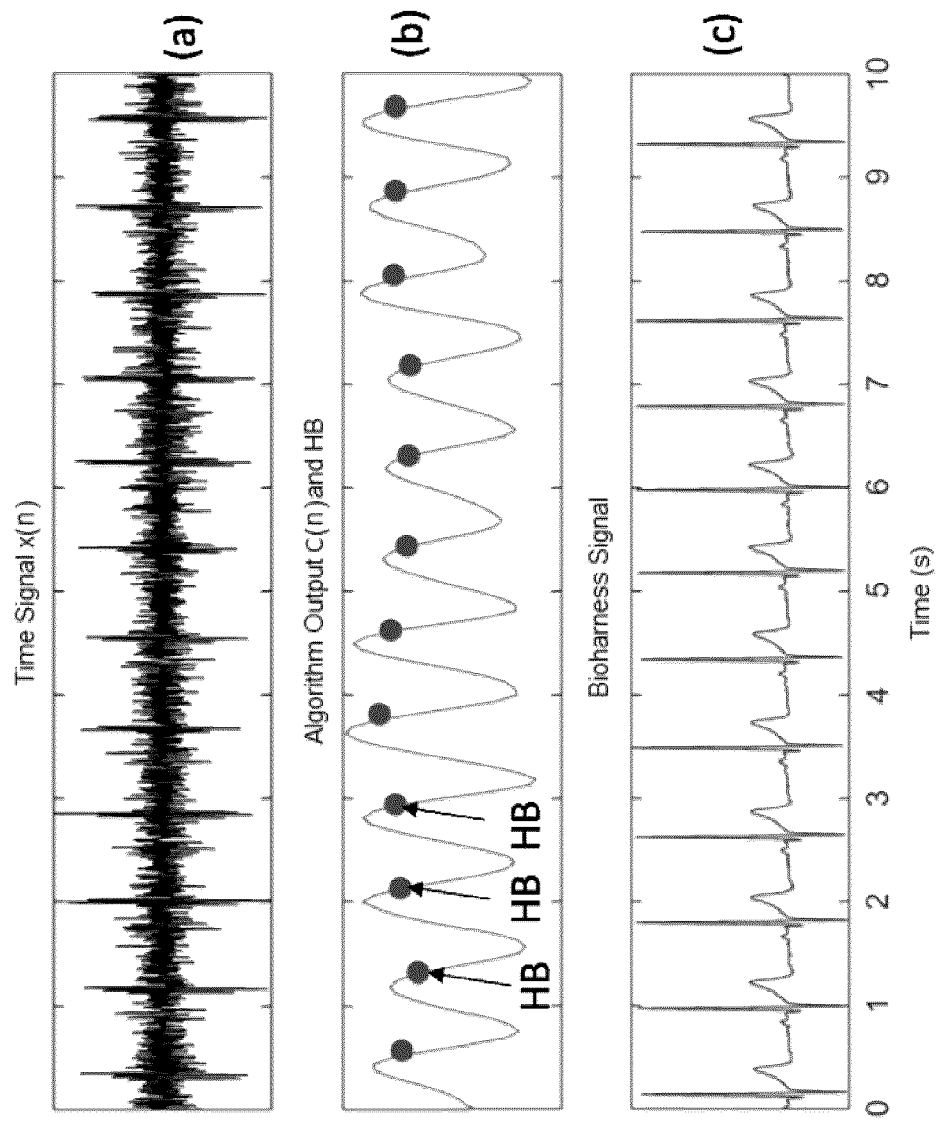
FIG. 7 shows: (a) measured and recorded audio time signal showing clear peaks for heartbeats; (b) output of the heart rate extraction algorithm for the recorded audio signal; (c) reference signal from BioHarness™.

FIG. 7 shows: (a) recorded audio time signal showing clear peaks for heartbeats; (b) output of the heart rate extraction algorithm for the recorded audio signal; (b) reference signal from BioHarness™. The dots at FIG. 7 (*b*) show the detected heartbeats (HB), showing good agreement with the reference signal.

In particular, FIG. 7 shows an audio signal of normal breathing measured by the IEM, x(n), the output signal of the algorithm, C (n), with the heartbeats detected by the algorithm (HB), and the time signal from the wearable chest belt (BioHarness™).

Figure 8:
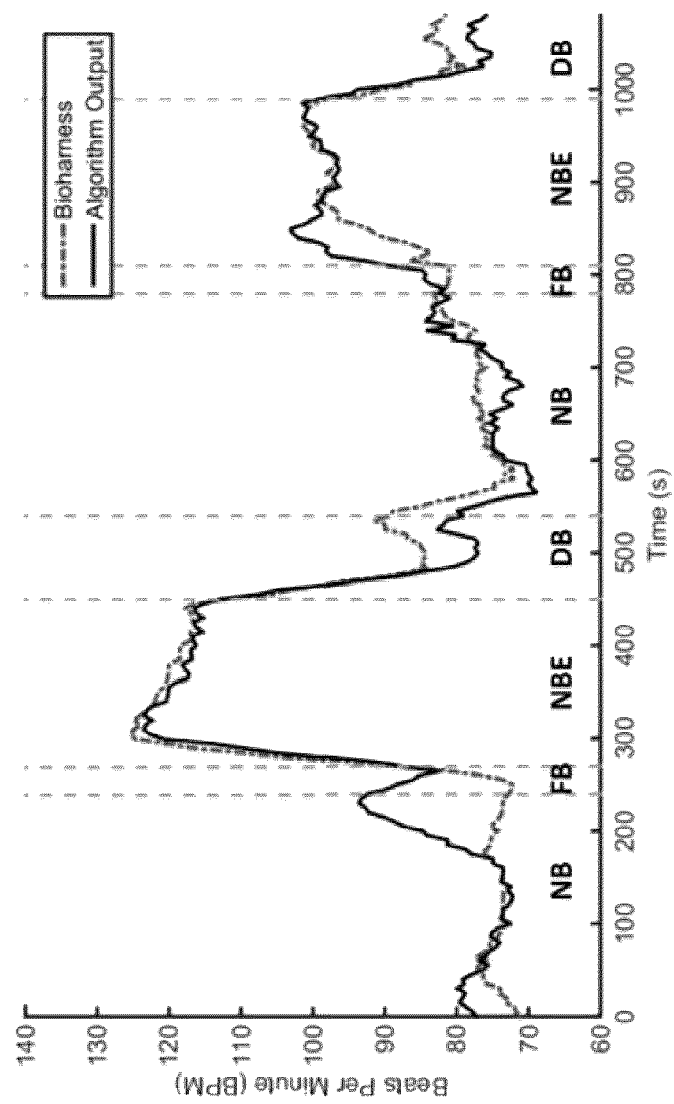
FIG. 8 shows comparison between the reference heart rate and the output of the algorithm developed for 8 types of respiration over 18 minutes (in one ear)

The evolution of the heart rate over time is presented in FIG. 8 for one subject over a sequence of 18 minutes. Shown at FIG. 8 is a comparison between the reference heart rate and the output of the algorithm developed for 8 types of respiration over 18 minutes (in one ear). Vertical lines indicate separations between the respiration types: four mouth breathing followed by four nose breathings. The generally good agreement between the two curves was obtained in this example, with a mean absolute error of 4.0 BPM.

The absolute error was computed as the difference between the reference rhythm and the algorithm output rhythm. The average absolute error over the entire 18 minutes of recording for this subject was 4.0 BPM. The routine for computing heart rate from heart beats detected by the algorithm induced a delay on the curves when the respiration type changed.

For heart rate extraction, the mean absolute error for the 20 subjects, computed as the mean of all the individual absolute errors & defined above, was 4.3 BPM, with a standard deviation of 2.2 BPM. This gave a mean relative error of 5.6%, with a relative standard deviation of 51.2%, computed as the ratio in percentage (%) between the standard deviation and the mean.

Figure 9:
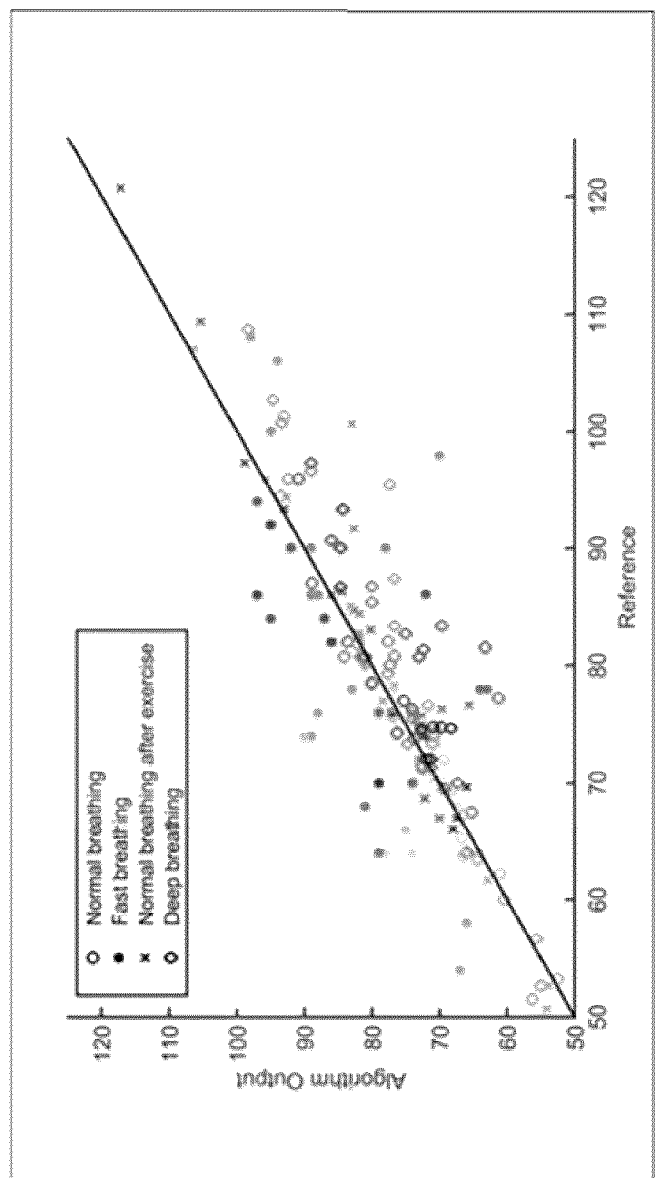
FIG. 9 shows scatter plot of heart rate for the algorithm output over the reference device.

FIG. 9 shows a scatter plot of heart rate for the algorithm output over the reference device. In particular, FIG. 9 is a scatter plot of the mean heart rate obtained for each respiration condition for each subject. Mean value for both ears of the heart rate for each respiration type (one color per subject, mouth and nose breathing have the same symbol) was calculated.

The closer the points are to the line y=x, the better the algorithm performed. Algorithm output was close to the reference for most recordings. Good predictive capabilities of the algorithm on a wide range of BPM were obtained in this example.

Figure 10:
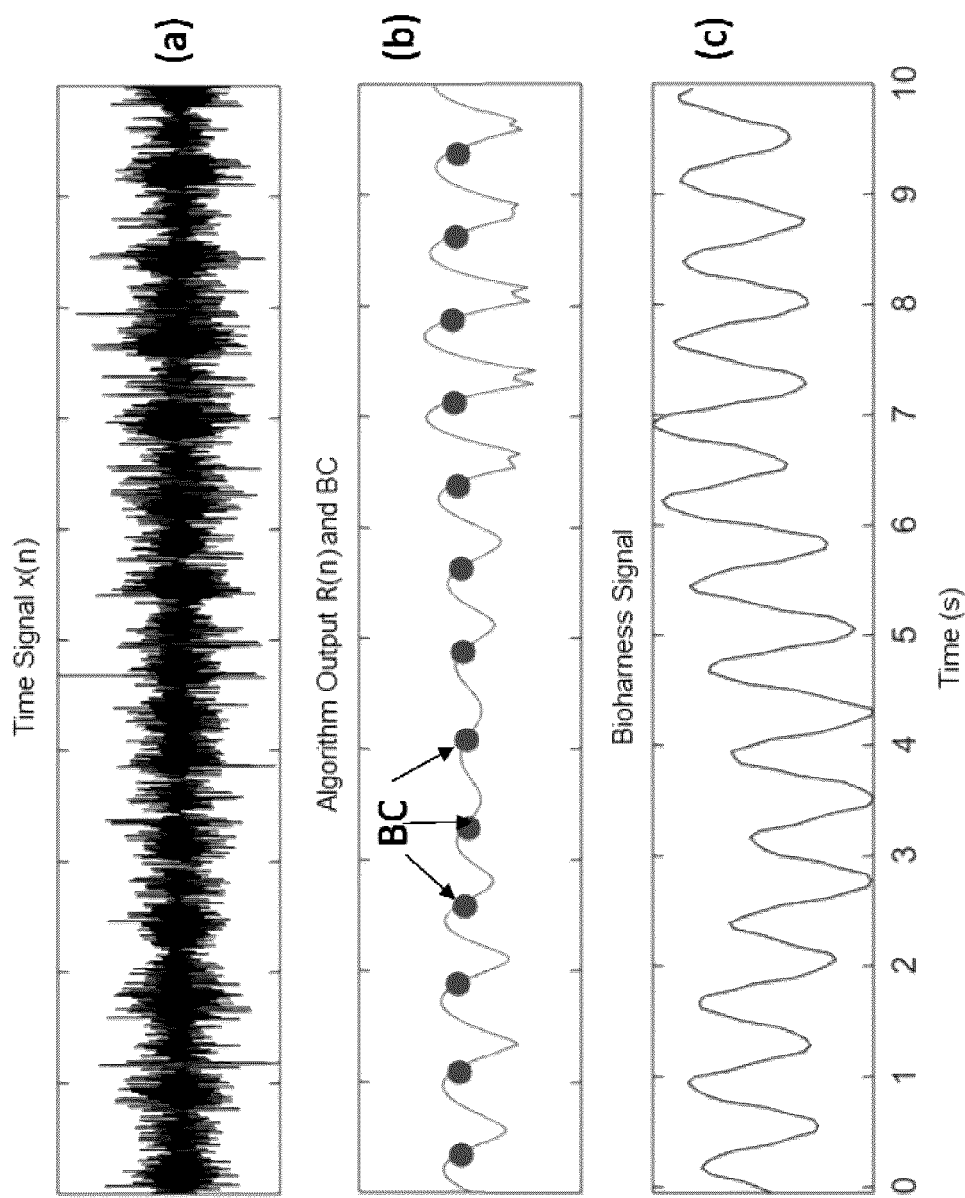
FIG. 10 shows: (a) recorded audio time signal of fast breathing; (b) output of the breathing rate extraction algorithm on recorded audio signal; (c) reference signal from BioHarness™.

FIG. 10 shows (a) recorded audio time signal of fast breathing measured by the IEM, x(n). FIG. 10 also shows (b) an output of the breathing rate extraction algorithm on recorded audio signal, i.e. the output signal of the algorithm R (n) with the breathing cycles detected by the algorithm (BC). Reference signal from BioHarness™ (c) is also shown. Detected breathing cycles were in good agreement with the reference signal in this example.

Figure 11:
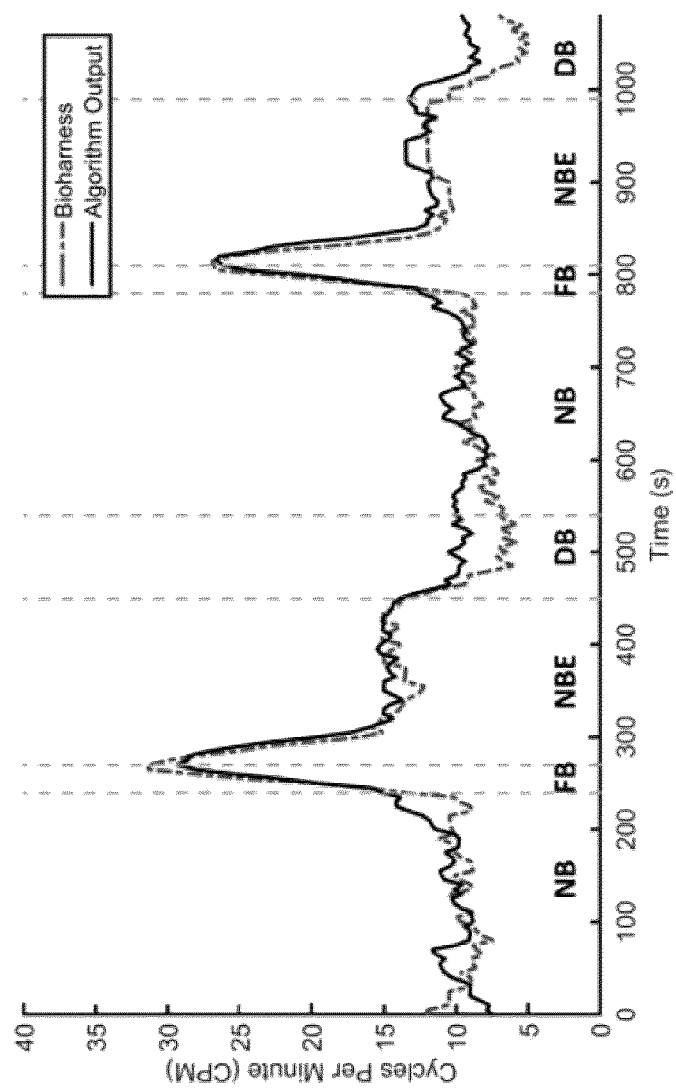
FIG. 11 shows comparison between the reference breathing rate and the output of the algorithm developed for 8 types of respiration over 18 minutes (in one ear)

The evolution of the breathing rate over time is shown in FIG. 11 for one subject over a sequence of 18 minutes. In particular, FIG. 11 shows comparison between the reference breathing rate and the output of the algorithm developed for 8 types of respiration over 18 minutes (in one ear), showing general agreement between the two curves. Mean absolute error was 1.7 CPM. Vertical lines in FIG. 11 indicate separations between the respiration types: four mouth breathing followed by four nose breathings.

The average absolute error for this subject was 1.7 CPM. The routine for computing breathing rate from cycles detected by the algorithm induced a delay on the curves when the respiration type changed.

For breathing rate extraction, the mean absolute error for 20 subjects was 3.0 CPM, with a standard deviation of 1.5 CPM. This gave a mean relative error of 25.1%, with a relative standard deviation of 50%.

Figure 12:
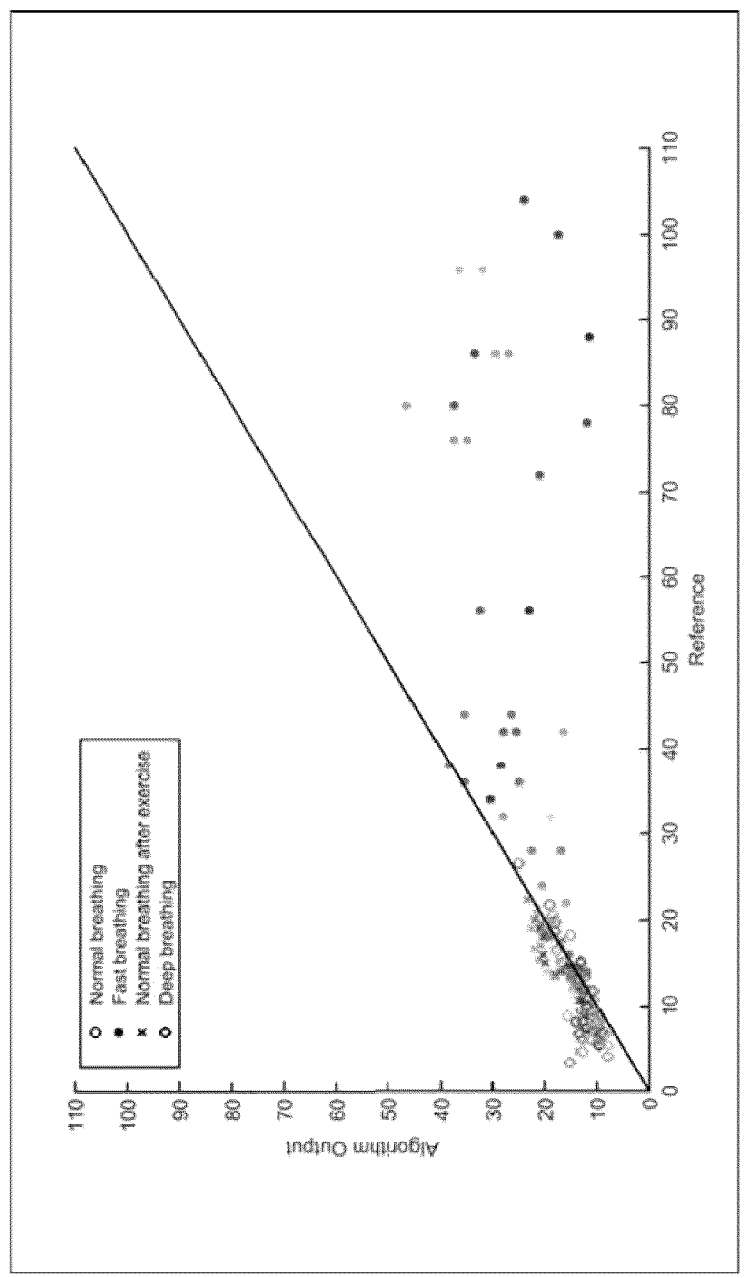
FIG. 12 shows a scatter plot of the breathing rate for the algorithm output over the reference device, measured and determined using an embodiment of the system and method as described herein.

FIG. 12 shows a scatter plot of the breathing rate for the algorithm output over the reference device. In particular, FIG. 12 shows a scatter plot of the mean breathing rate obtained for each respiration condition for each subject. Mean value for both ears of breathing rate for each respiration type (one color per subject, mouth and nose breathing have the same symbol) was calculated.

Algorithm output was close to the reference for low values of the breathing rate under 25 CPM, demonstrating good predictive capabilities of the algorithm on a breathing rate of fewer than 25 CPM in this example.

Denoising of Biosignals from Ambient Noise

This section presents the results of the proposed extraction algorithms for heart and breathing rates when noise was added to the signal, as described herein.

Figure 13:
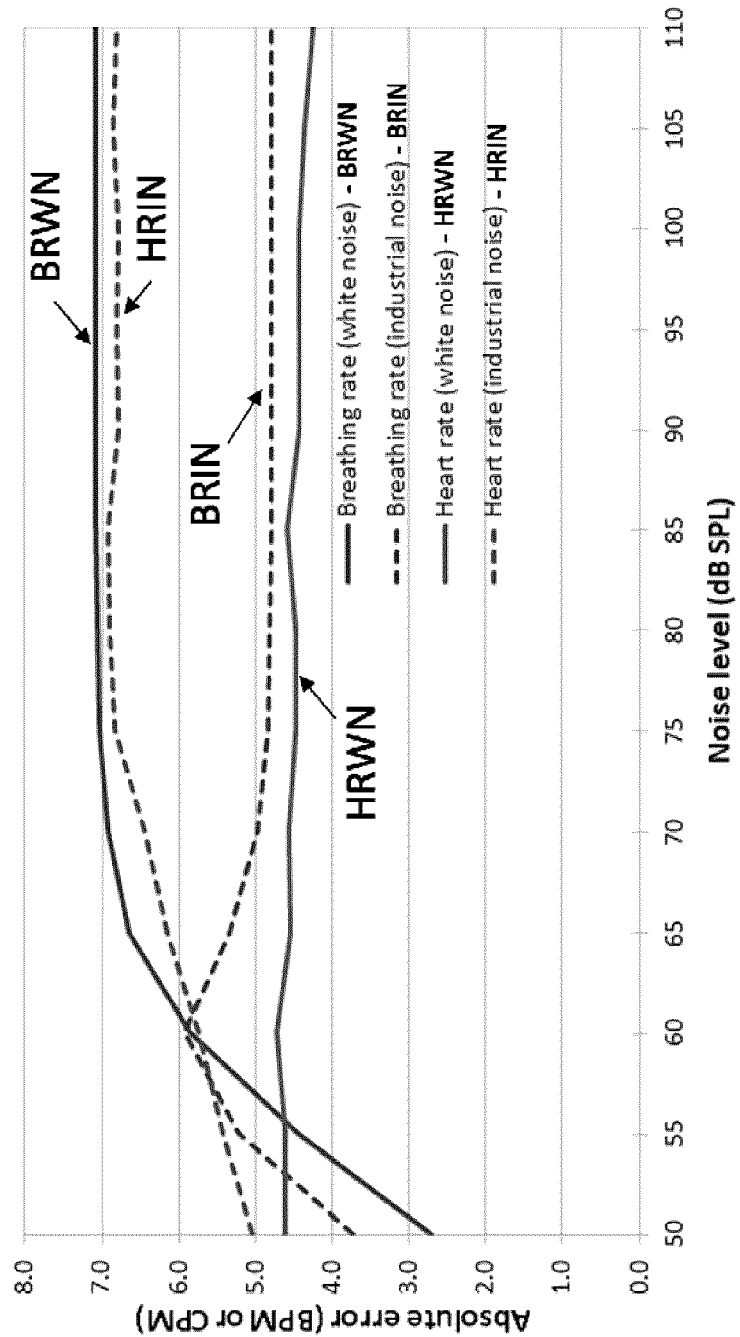
FIG. 13 shows evolution of absolute error averaged for 20 subjects as a function of noise level.

FIG. 13 shows evolution of absolute error averaged for 20 subjects as a function of noise level, showing good performance for heart rate extraction with broadband white and industrial noise in this example. The increase in the error is greater for breathing rate extraction with white and industrial noise.

Figure 14:
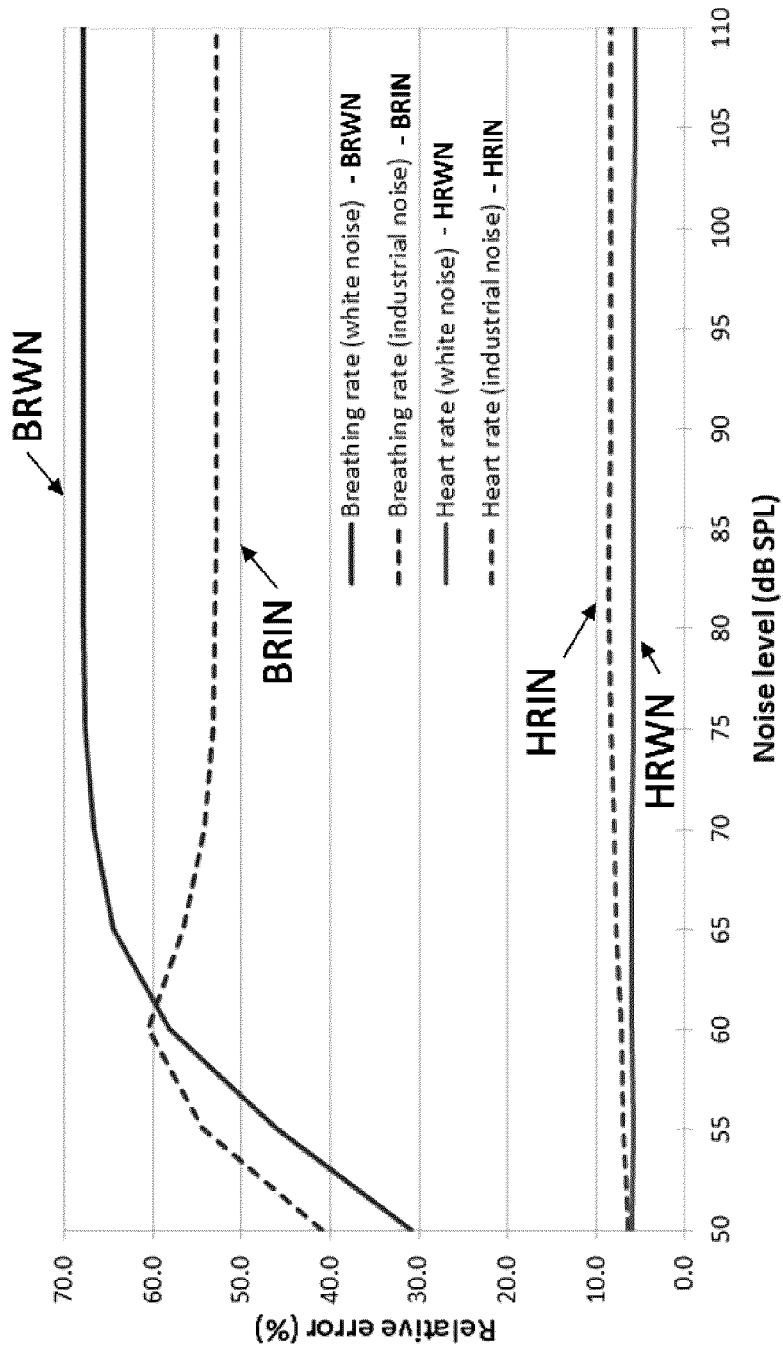
FIG. 14 shows evolution of relative error averaged for 20 subjects as a function of noise level.

FIG. 14 shows evolution of relative error averaged for 20 subjects as a function of noise level, showing good performance for heart rate extraction with white and industrial noise in this example. The increase in the error may be greater for breathing rate extraction than for the heart rate.

FIG. 13 and FIG. 14 show the evolution (for the 20 subjects) of the mean absolute error and the mean relative error respectively, when the signal is corrupted by noise at levels ranging from 50 to 110 dB SPL. For the heart rate, the absolute error did not exceed 4.7 BPM for broadband white noise (6.1% relative error) and 7.6 BPM for industrial noise (9.1% relative error). With white noise, errors plateaued from 50 dB up to 110 dB. With industrial noise, errors increased up to 85 dB and then plateaued up to 110 dB.

For the breathing rate, the absolute error did not exceed 7.4 CPM for white noise (63.9% relative error) and 6.6 CPM for industrial noise (57.9% relative error). With white noise, errors increased until 75 dB and then plateaued up to 110 dB. With industrial noise, errors increased until 60 dB then plateaued from 65 dB to 110 dB.

Experimental results showed an accurate extraction of heart rate for 20 subjects. The mean absolute error was 4.3 BPM (5.6% relative error).

Extraction of the breathing rate was less accurate, with an absolute error of 3.0 CPM (25.1% relative error). For some subjects, the extraction worked very well as shown in FIG. 11.

This simulation was performed offline, without actually running the algorithms while the subject was exposed to the noise source (either white or industrial noise) and was performed to assess the robustness of the algorithms against noise. The denoising using adaptive filtering as described herein was used to denoise acoustic biosignals measured inside the ear canal.

For the heart rate extraction, simulation results showed a very small increase in the absolute error. The denoising filtering performed well in low frequency. The absolute error did not exceed 4.7 BPM for white noise and 7.6 BPM for industrial noise, which represented low relative errors (respectively 6.1% and 9.1%). The industrial noise had a higher energy in the band of 20 to 120 Hz than the white noise and consequently affected the detection in low frequency for heartbeats.

For the breathing rate extraction, simulation results showed an increase in the absolute error. The results of this example showed that the denoising filter may perform sufficiently well below 65 dB SPL.

The absolute errors increased until 7.4 CPM for white noise and 6.6 CPM for industrial noise, which represented high relative errors (63.9% and 57.9% respectively). The extraction algorithm performed was less efficient with a signal free from ambient noise. Typically, industrial noise has tonal components in its spectrum, which distinguishes it from the breathing spectrum in the band of interest, namely 150 to 400 Hz. White noise (same energy at all frequencies)

has a similar spectrum to that of breathing for some subjects in the band of interest. This is why the denoising process may be more efficient with industrial noise than with white noise.

In the example described herein, the mean absolute errors for the 20 subjects were 4.3 beats per minute (BPM) for heart rate and 3.0 cycles per minute (CPM) for breathing rate. The robustness of the algorithms was assessed against ambient noise. Broad band white noise and industrial noise were added numerically to the in-ear signal. An nLMS adaptive filter was used to remove the unwanted noise.

In this example, for noise of up to 110 dB SPL the heart rate was extracted with absolute errors below 7.6 BPM (9.1% relative error), whereas the extraction of the breathing rate with noise was less accurate: with absolute errors lower than 7.4 CPM (63.9% relative error). In this example, the algorithm (especially for heart rate) has shown to have low sensitivity to simulated high noise environments.

While illustrative and presently preferred embodiments of the invention have been described in detail hereinabove, it is to be understood that the inventive concepts may be otherwise variously embodied and employed and that the appended claims are intended to be construed to include such variations except insofar as limited by the prior art.

The invention claimed is:

1. A computer-implemented method for determining an attribute of a heart rate or breathing rate, the method comprising:
    capturing at least one inner audio signal inside an at least partially occluded ear canal with an in-ear microphone of an earpiece worn in the occluded ear canal of an active user;
    capturing an outer audio signal with an outer-ear microphone of the earpiece, the outer audio signal being indicative of sounds captured from the environment outside the ear canal;
    using an adaptive filter to compute an estimated residual signal of the environment present in the occluded ear canal using the outer audio signal;
    denoising the at least one inner audio signal based on the estimated residual signal; and
    using a processing device to determine a measurement of at least one of a heart rate and a breathing rate based on the denoised inner audio signal by extracting at least one of the heart rate and the breathing rate from the at least one inner audio signal, the extraction further comprising:
    applying a first band pass filter on the at least one inner audio signal;
    applying a Hilbert transform to extract the envelope of the filtered inner audio signal;
    calculating ratios between one or more maxima of the spectrum of the extracted envelope;
    determining a center frequency of a second band pass filter from the calculated ratios;
    applying the second band pass filter on the filtered audio signal to produce a filtered signal; and
    extracting the peaks of the filtered signal.

2. The method of claim 1 wherein an attribute of the at least one inner audio signal is indicative of a state selected from the group consisting of a health state, an emotional state, an activity state and a general state.

3. The method of claim 1 wherein an attribute of the at least one inner audio signal is indicative of a measurement of the at least one inner audio signal.

4. The method of claim 1 wherein the extracting further comprises a first decimation before applying the first band pass filter and a second decimation before determining the center frequency of the second band pass filter.

5. The method of claim 1 wherein the adaptive filter denoises the at least one inner audio signal by applying higher relative weights for the filter coefficients of the adaptive filter at frequencies matching frequencies of the at least one inner audio signal.

6. The method of claim 1, the denoising of the at least one inner audio signal further comprising subtracting the estimated residual signal from the captured inner audio signal.

7. The method of claim 1 wherein the determination of the center frequency further comprises calculating the spectrum of the extracted envelope and calculating an average between left and right ears.

8. The method of claim 1 wherein the determination of the center frequency is based on the calculation of ratios between three maxima of the spectrum of the extracted envelope.

* * * * *